US008435181B2

(12) United States Patent
Yang et al.

(10) Patent No.: US 8,435,181 B2
(45) Date of Patent: May 7, 2013

(54) SYSTEM AND METHOD TO IDENTIFY AND MEASURE ORGAN WALL BOUNDARIES

(75) Inventors: Fuxing Yang, Woodinville, WA (US); Stephen Dudycha, Bothell, WA (US); Gerald McMorrow, Redmond, WA (US)

(73) Assignee: Verathon Inc., Bothell, WA (US)

( * ) Notice: Subject to any disclaimer, the term of this patent is extended or adjusted under 35 U.S.C. 154(b) by 0 days.

(21) Appl. No.: 12/882,017

(22) Filed: Sep. 14, 2010

(65) Prior Publication Data

US 2011/0004101 A1 Jan. 6, 2011

Related U.S. Application Data

(63) Continuation of application No. 11/625,805, filed on Jan. 22, 2007, now Pat. No. 7,819,806.

(51) Int. Cl.
*A61B 8/00* (2006.01)

(52) U.S. Cl.
USPC .......... 600/443; 600/437; 600/449; 600/447; 73/625; 73/626

(58) Field of Classification Search .................. 600/407, 600/437, 443, 449, 447; 73/625, 626
See application file for complete search history.

(56) References Cited

U.S. PATENT DOCUMENTS

| 6,106,465 | A  | * | 8/2000 | Napolitano et al. | 600/443 |
|---|---|---|---|---|---|
| 6,264,609 | B1 | * | 7/2001 | Herrington et al. | 600/443 |
| 6,585,647 | B1 | * | 7/2003 | Winder | 600/437 |

\* cited by examiner

*Primary Examiner* — Brian Casler
*Assistant Examiner* — Joel Lamprecht
(74) *Attorney, Agent, or Firm* — Scott Born; Foster Pepper PLLC

(57) ABSTRACT

Systems and methods are described for acquiring, processing, and presenting boundaries of a cavity-tissue interface within a region-of-interest in an ultrasound image based upon the strength of signals of ultrasound echoes returning from structures within the region-of-interest. The segmentation of boundaries of cavity shapes occupying the region-of-interest utilizes cost function analysis of pixel sets occupying the cavity-tissue interface. The segmented shapes are further image processed to determine areas and volumes of the organ or structure containing the cavity within the region-of-interest.

7 Claims, 35 Drawing Sheets

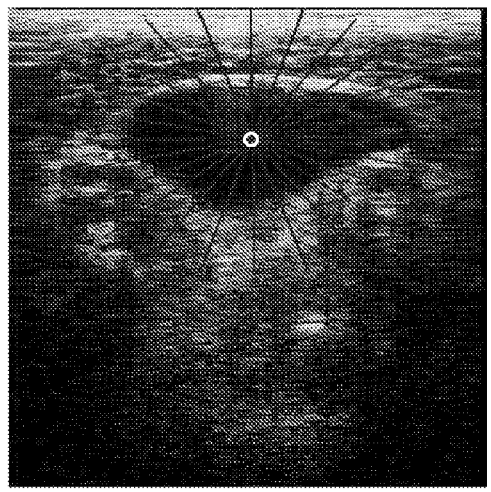
*Fig. 21*
A
B
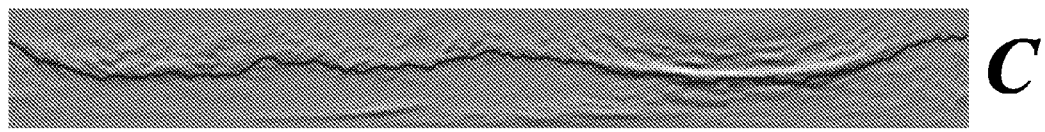
C
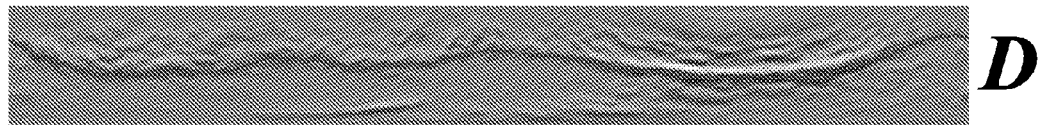
D
*Figs. 22A-D*

Fast Marching Method Applied to Pixel Grid

○ Far
× Trial
● Accepted
⊗ Minimal Arrival Time $X_m$

Point $X_m$ has minimum arrival time among all trial points, which will be moved to the accepted set and the arrival times of neighbors are updated.

Bladder Phantom Segmentations
Initial Walls | Dynamic Programming
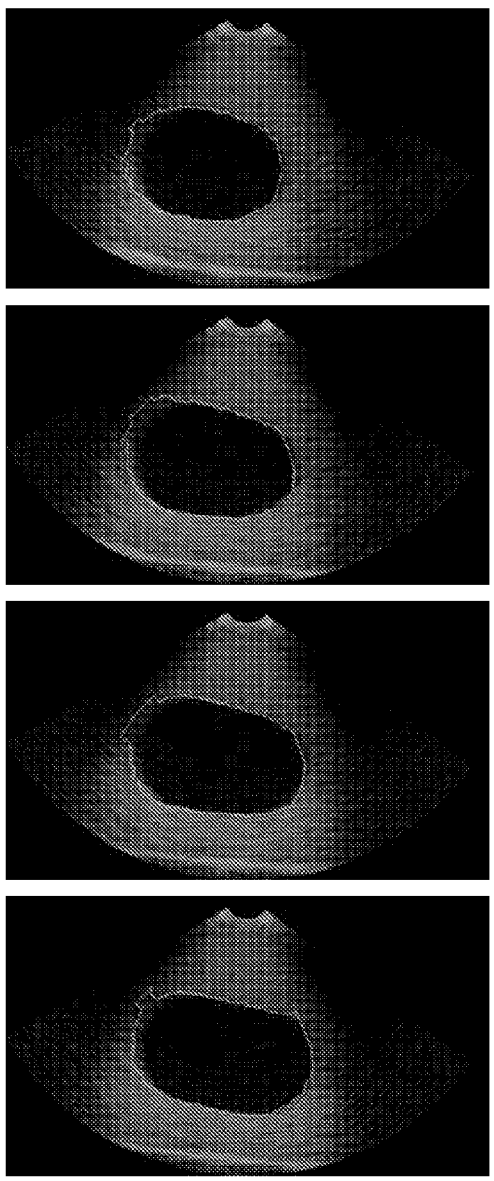
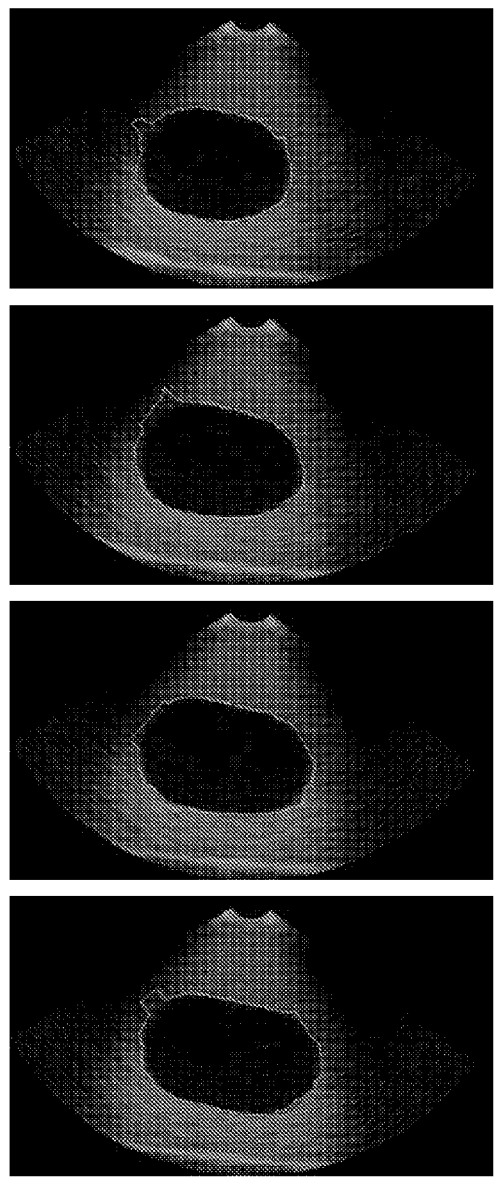
*Fig. 34A* | *Fig. 35A*

Bladder Phantom Segmentations
Initial Walls | Dynamic Programming
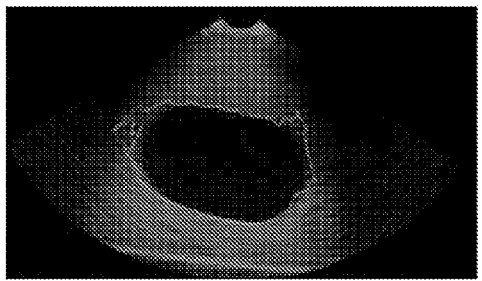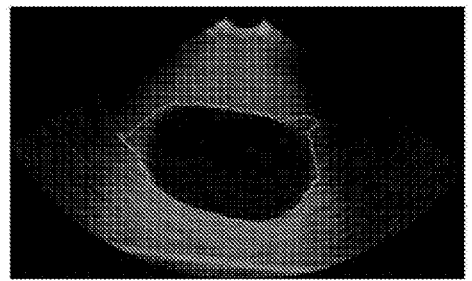
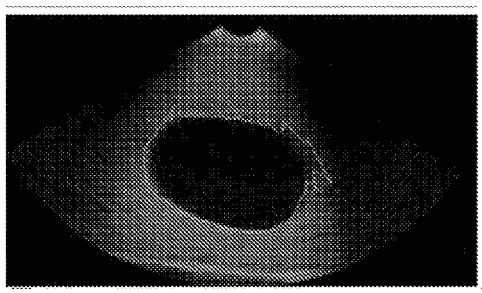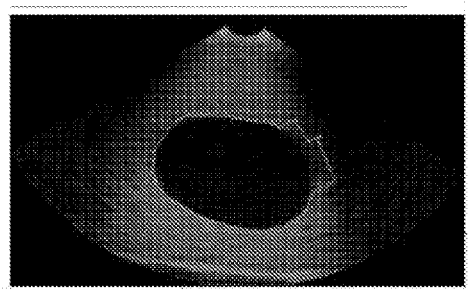
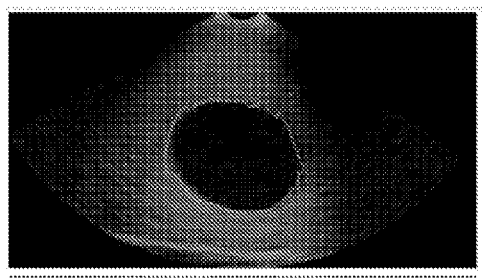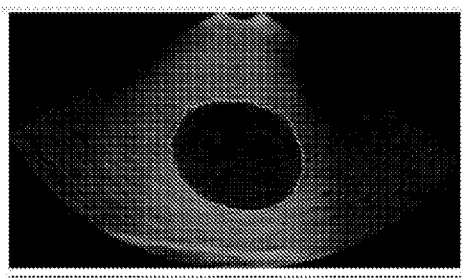
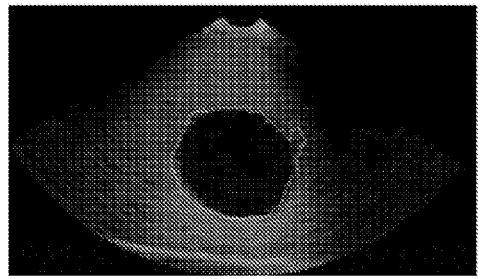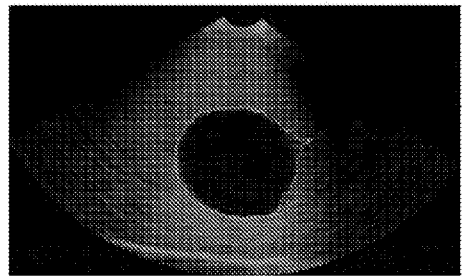
*Fig. 34B* | *Fig. 35B*

Bladder Segmentations
Initial Walls | Dynamic Programming
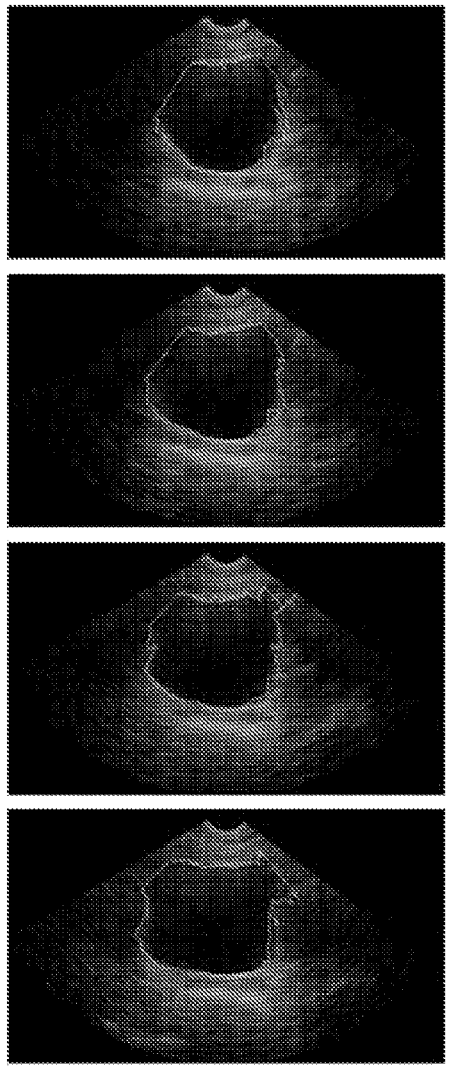
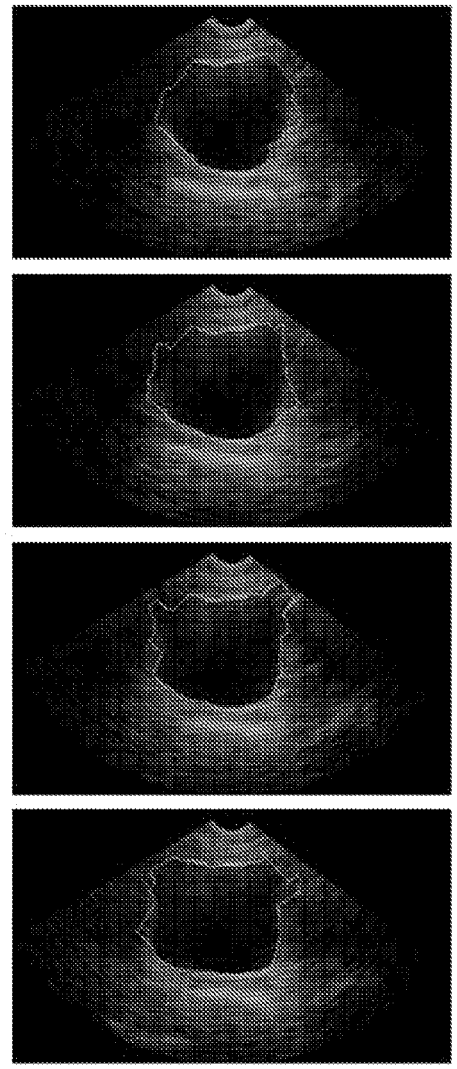
*Fig. 36A* | *Fig. 37A*

Bladder Segmentations
Initial Walls
Dynamic Programming
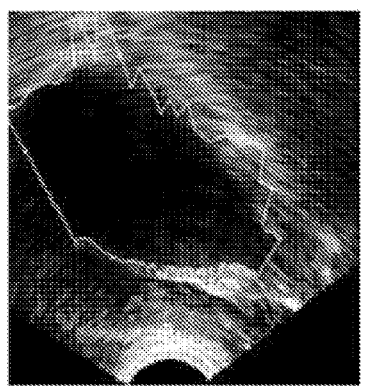
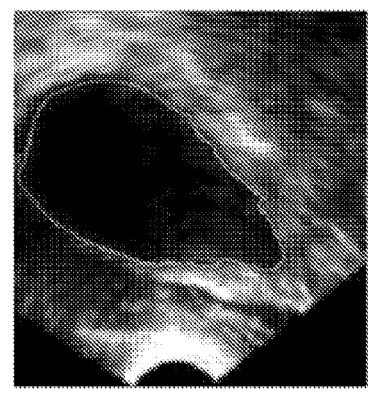
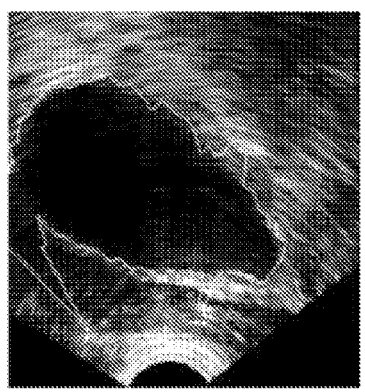
*Fig. 36B*　　　　*Fig. 37B*

Bladder Segmentations

Initial Walls · Dynamic Programming

Segmentation + original image

The 3D centerline based on EDT and starting and ending points

3D EDT (Euclidian Distance Transform)

The perpendicular planes along the centerline

SYSTEM AND METHOD TO IDENTIFY AND MEASURE ORGAN WALL BOUNDARIES

RELATED APPLICATIONS

This application is a continuation of U.S. patent application Ser. No. 11/625,805 filed Jan. 22, 2007 entitled "SYSTEM AND METHOD TO IDENTIFY AND MEASURE ORGAN WALL BOUNDARIES," which is hereby incorporated herein by reference.

This application incorporates by reference and claims priority to U.S. provisional patent application Ser. No. 60/882,888 filed Dec. 29, 2006.

This application incorporates by reference and claims priority to U.S. provisional patent application Ser. No. 60/828,614 filed Oct. 6, 2006.

This application incorporates by reference and claims priority to U.S. provisional patent application Ser. No. 60/760,677 filed Jan. 20, 2006.

This application is a continuation-in-part of and claims priority to U.S. patent application Ser. No. 11/213,284 filed Aug. 26, 2005.

This application claims priority to and is a continuation-in-part of U.S. patent application Ser. No. 11/119,355 filed Apr. 29, 2005, which claims priority to U.S. provisional patent application Ser. No. 60/566,127 filed Apr. 30, 2004. This application also claims priority to and is a continuation-in-part of U.S. patent application Ser. No. 10/701,955 filed Nov. 5, 2003, which in turn claims priority to and is a continuation-in-part of U.S. patent application Ser. No. 10/443,126 filed May 20, 2003.

This application claims priority to and is a continuation-in-part of U.S. patent application Ser. No. 11/061,867 filed Feb. 17, 2005, which claims priority to U.S. provisional patent application Ser. No. 60/545,576 filed Feb. 17, 2004 and U.S. provisional patent application Ser. No. 60/566,818 filed Apr. 30, 2004.

This application is also a continuation-in-part of and claims priority to U.S. patent application Ser. No. 11/222,360 filed Sep. 8, 2005.

This application is also a continuation-in-part of and claims priority to U.S. patent application Ser. No. 11/061,867 filed Feb. 17, 2005.

This application is also a continuation-in-part of and claims priority to U.S. patent application Ser. No. 10/704,966 filed Nov. 10, 2004.

This application claims priority to and is a continuation-in-part of U.S. patent application Ser. No. 10/607,919 filed Jun. 27, 2005.

This application is a continuation-in-part of and claims priority to PCT application serial number PCT/US03/24368 filed Aug. 1, 2003, which claims priority to U.S. provisional patent application Ser. No. 60/423,881 filed Nov. 5, 2002 and U.S. provisional patent application Ser. No. 60/400,624 filed Aug. 2, 2002.

This application is also a continuation-in-part of and claims priority to PCT Application Serial No. PCT/US03/14785 filed May 9, 2003, which is a continuation of U.S. patent application Ser. No. 10/165,556 filed Jun. 7, 2002.

This application is also a continuation-in-part of and claims priority to U.S. patent application Ser. No. 10/888,735 filed Jul. 9, 2004.

This application is also a continuation-in-part of and claims priority to U.S. patent application Ser. No. 10/633,186 filed Jul. 31, 2003 which claims priority to U.S. provisional patent application Ser. No. 60/423,881 filed Nov. 5, 2002 and to U.S. patent application Ser. No. 10/443,126 filed May 20, 2003 which claims priority to U.S. provisional patent application Ser. No. 60/423,881 filed Nov. 5, 2002 and to U.S. provisional application 60/400,624 filed Aug. 2, 2002. All of the above applications are incorporated by reference in their entirety as if fully set forth herein.

FIELD OF THE INVENTION

An embodiment of the invention relates generally to ultrasound-based diagnostic systems and procedures employing image acquisition, processing, and image presentation systems and methods.

BACKGROUND OF THE INVENTION

Computer based analysis of medical images pertaining to ascertaining organ structures allows for the diagnosis of organ diseases and function. Identifying and measuring organ boundaries allows a medical expert to access disease states and prescribe therapeutic regimens. The true shape a cavity or structure within body tissue requires accurate detection for the medical expert to assess organ normalcy or pathological condition. However, inaccurate border detection, as shown in the inaccurately segmented bladder cavities of FIGS. 5 and 6 in which the bladder cavity border significantly overlaps into surrounding echogenic tissue to overestimate the bladder cavity size, or carves out a lumen area to underestimate the bladder size. Thus a false internal boundary is presented and prevents an accurate assessment of a true medical condition since the bladder cavity area and volume is either underestimated or overestimated. There is a need to non-invasively identify and accurately measure cavity boundaries within an ultrasound probed region-of-interest to accurately access a medical condition.

SUMMARY OF THE PARTICULAR EMBODIMENTS

Ultrasound systems and methods to dynamically develop and present 2D and 3D images of a cavity structure within a region-of-interest (ROI) that is either partially or completely surrounded by echogenic tissue to permit the accurate detection and delineation of close contours of a cavity-tissue interface in the wall region of an organ or structure. The ultrasound systems and algorithmic methods are adapted to detect and segment cavities according to the shape of the cavity and the degree to which the cavity is surrounded by higher echogenic tissue by dynamically analyzing pixel groups near the cavity-tissue interface. The transceivers used by the ultrasound systems vary in the fundamental frequency used for probing the ROI. The algorithms vary as to which fundamental or harmonic frequency is used for imaging and whether the cavity is substantially spherical or substantially non-spherical.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee. Embodiments for the system and method to develop, present, and use a color-coded image of a structure within a region-of-interest are described in detail below with reference to the following drawings.

FIG. 21 is an image of a bladder cavity to determine the pixel center of the bladder cavity;

FIGS. 22A-D illustrates a sequence of images obtained from application of dynamic processing sub-algorithms 378 and 378G of FIGS. 17 and 18;

FIGS. 34A-B are linearly interpolated segmentations of bladder phantom ultrasound images;

FIGS. 35A-B are fast marching-live wire segmentations of bladder phantom ultrasound images in relation to the same bladder images of FIGS. 29A-B;

FIGS. 36A-C is a series of Cartesian bladder images segmented by non-fast marching-live wire algorithms;

FIG. 37A-C is a series of Cartesian bladder images segmented by the fast marching-live wire algorithms of processing block 300 illustrated in FIG. 7;

DETAILED DESCRIPTION OF THE PREFERRED EMBODIMENTS

Figure 1:
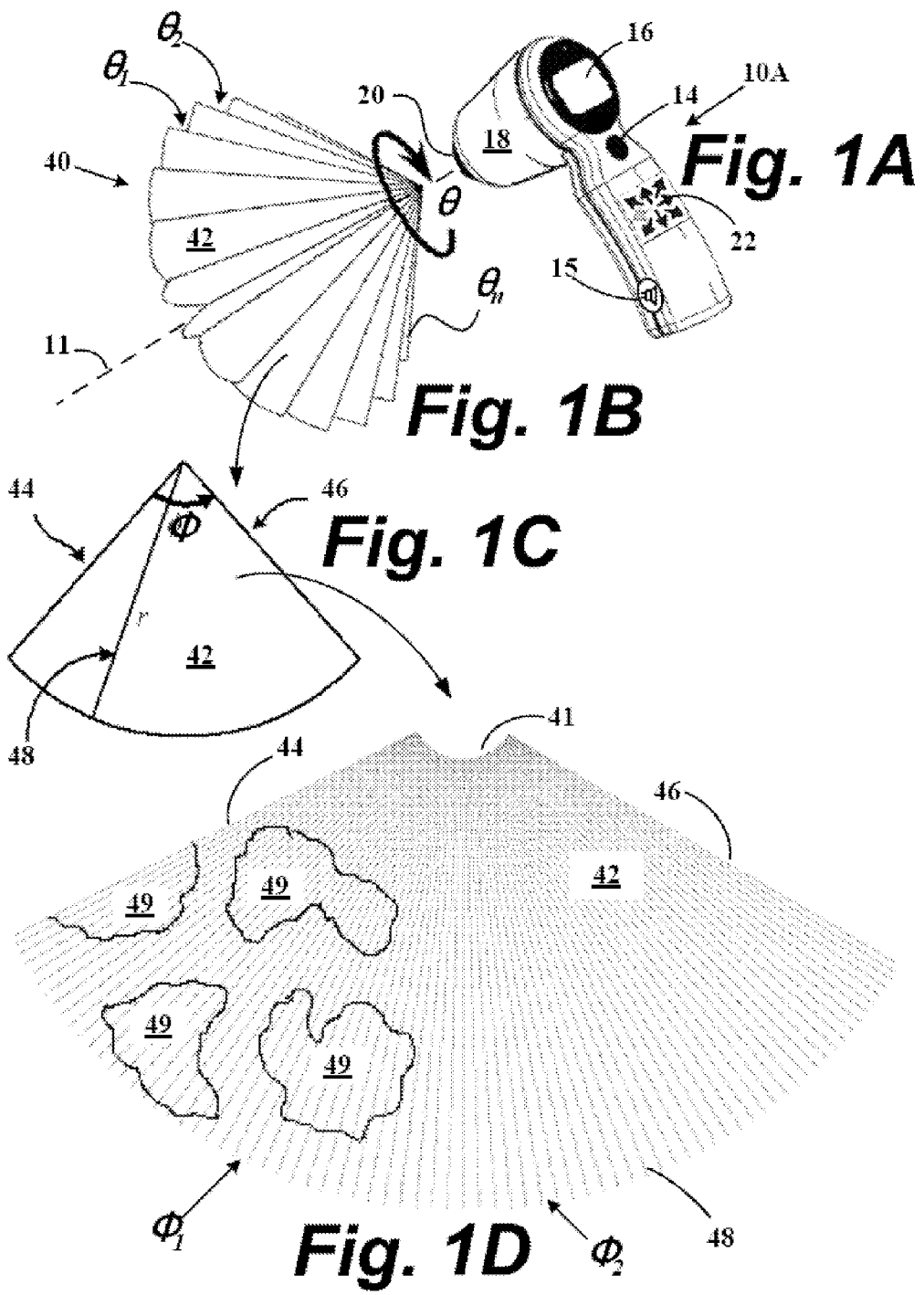
FIGS. 1A-D depicts a partial schematic and a partial isometric view of a transceiver, a scan cone comprising a rotational array of scan planes, and a scan plane of the array of an ultrasound harmonic imaging system.

Systems and methods are described acquiring, processing, and presenting a ultrasound images based upon the strength of signals from a selected fundamental or harmonic frequency returning from cavity structures within a region-of-interest having substantially spherical or substantially non-spherical shapes. Alternate embodiments include ultrasound systems and algorithmic methods to detect and segment spherically shaped bladders having dimly illuminated to dark pixels in the shadow regions residing near cavity-tissue interface that is surrounded by brighter echogenic tissue. The shadow region makes boundary detection difficult in 2D systems as pixel candidate selection can be error prone and any algorithm dependent upon initial pixel candidate selection will carry forward any error, and possibly amplify the error if successor pixel candidates also happen to be improperly selected. Other alternate embodiments include ultrasound systems and methods adapted to detect and segment non-spherical cavities that are partially enveloped in echogenic tissue, for example tubular or cylindrical shaped blood vessels, for example, the abdominal aorta, and any bulges thereto that would be diagnostic for an aneurysm. Components that exhibit differing echogenic and signal absorbing characteristics for the selected imaging harmonic frequency. Optimization of image acquisition by providing system and methods to direct transceiver placement or repositioning is described. The segmentation of boundaries of shapes for structures within the region-of-interest of an image or series of images using the selected imaging harmonic frequency is described and to classify an organ of interest, for example, a bladder, into large or small bladders. The latter being optionally advantageous in determining whether catheterization is required. The segmented shapes may be further image processed to determine thicknesses, areas, volumes, masses and changes thereof for the structure of interest.

When the structure or organ of interest, or region of interest (ROI) is a bladder, classification results may be applied to alert the computer executable programs to check either or any combination of the volume measurement to properly classify a small or large bladder, the volume measurement of the bladder if more than 150 ml, the male or female gender of the subject, and to adjust segmentation algorithms to prevent overestimation of the bladder size.

The result can be also be combined with pseudo C-mode view displaying for aiming or final bladder shape. The simplest way to utilize the result may be that if the bladder size is large based on harmonic ratio classification, we can check the dimension of current shape (no matter for aiming or for final shape), if it is too small, an appropriate compensation can be added to enlarge the size of the shape for displaying; if the size is small, we can give an appropriate penalty to the shape.

Alternate embodiments include systems and methods for acquiring, processing, and presenting boundaries of a cavity-tissue interface within a region-of-interest in an ultrasound image based upon the strength of signals of ultrasound echoes returning from structures within the region-of-interest. The segmentation of boundaries of cavity shapes occupying the region-of-interest utilizes cost function analysis of pixel sets occupying the cavity-tissue interface. The segmented shapes may be further image processed to determine areas and volumes of the organ or structure containing the cavity within the region-of-interest.

Yet other alternate embodiment include systems and/or methods of image processing are described for automatically segmenting, i.e. automatically detecting the boundaries of shapes within a region of interest (ROI) of a single or series of images undergoing dynamic change. Particular and alternate embodiments provide for the subsequent measurement of areas and/or volumes of the automatically segmented shapes within the image ROI of a singular image multiple images of an image series undergoing dynamic change.

Methods include creating an image database having manually segmented shapes within the ROI of the images stored in the database, training computer readable image processing algorithms to duplicate or substantially reproduce the appearance of the manually segmented shapes, acquiring a non-database image, and segmenting shapes within the ROI of the non-database image by using the database-trained image processing algorithms.

In particular, as applied to sonographic systems, ultrasound systems and/or methods employing the acquisition of 3D sonograms based upon the optimal harmonic for a given tissue structure.

FIGS. 1A-D depicts a partial schematic and a partial isometric view of a transceiver, a scan cone comprising a rotational array of scan planes, and a scan plane of the array of various ultrasound harmonic imaging systems 60A-D illustrated in FIGS. 3 and 4 below.

FIG. 1A is a side elevation view of an ultrasound transceiver 10A that includes an inertial reference unit, according to an embodiment of the invention. The transceiver 10A includes a transceiver housing 18 having an outwardly extending handle 12 suitably configured to allow a user to manipulate the transceiver 10A relative to a patient. The handle 12 includes a trigger 14 that allows the user to initiate an ultrasound scan of a selected anatomical portion, and a cavity selector 16. The cavity selector 16 will be described in greater detail below. The transceiver 10A also includes a transceiver dome 20 that contacts a surface portion of the patient when the selected anatomical portion is scanned. The dome 20 generally provides an appropriate acoustical impedance match to the anatomical portion and/or permits ultrasound energy to be properly focused as it is projected into the anatomical portion. The transceiver 10A further includes one, or preferably an array of separately excitable ultrasound transducer elements (not shown in FIG. 1A) positioned within or otherwise adjacent with the housing 18. The transducer elements may be suitably positioned within the housing 18 or otherwise to project ultrasound energy outwardly from the dome 20, and to permit reception of acoustic reflections generated by internal structures within the anatomical portion. The one or more array of ultrasound elements may include a one-dimensional, or a two-dimensional array of piezoelectric elements that may be moved within the housing 18 by a motor. Alternately, the array may be stationary with respect to the housing 18 so that the selected anatomical region may be scanned by selectively energizing the elements in the array.

A directional indicator panel 22 includes a plurality of arrows that may be illuminated for initial targeting and guiding a user to access the targeting of an organ or structure within an ROI. In particular embodiments if the organ or structure is centered from placement of the transceiver 10A acoustically placed against the dermal surface at a first location of the subject, the directional arrows may be not illuminated. If the organ is off-center, an arrow or set of arrows may be illuminated to direct the user to reposition the transceiver 10A acoustically at a second or subsequent dermal location of the subject. The acrostic coupling may be achieved by liquid sonic gel applied to the skin of the patient or by sonic gel pads to which the transceiver dome 20 is placed against. The directional indicator panel 22 may be presented on the display 54 of computer 52 in harmonic imaging subsystems described in FIGS. 3 and 4 below, or alternatively, presented on the transceiver display 16.

Transceiver 10A includes an inertial reference unit that includes an accelerometer 22 and/or gyroscope 23 positioned preferably within or adjacent to housing 18. The accelerometer 22 may be operable to sense an acceleration of the transceiver 10A, preferably relative to a coordinate system, while the gyroscope 23 may be operable to sense an angular velocity of the transceiver 10A relative to the same or another coordinate system. Accordingly, the gyroscope 23 may be of conventional configuration that employs dynamic elements, or it may be an optoelectronic device, such as the known optical ring gyroscope. In one embodiment, the accelerometer 22 and the gyroscope 23 may include a commonly packaged and/or solid-state device. One suitable commonly packaged device may be the MT6 miniature inertial measurement unit, available from Omni Instruments, Incorporated, although other suitable alternatives exist. In other embodiments, the accelerometer 22 and/or the gyroscope 23 may include commonly packaged micro-electromechanical system (MEMS) devices, which are commercially available from MEMSense, Incorporated. As described in greater detail below, the accelerometer 22 and the gyroscope 23 cooperatively permit the determination of positional and/or angular changes relative to a known position that is proximate to an anatomical region of interest in the patient. Other configurations related to the accelerometer 22 and gyroscope 23 concerning transceivers 10A,B equipped with inertial reference units and the operations thereto may be obtained from copending U.S. patent application Ser. No. 11/222,360 filed Sep. 8, 2005, herein incorporated by reference.

The transceiver 10A includes (or if capable at being in signal communication with) a display 24 operable to view processed results from an ultrasound scan, and/or to allow an operational interaction between the user and the transceiver 10A. For example, the display 24 may be configured to display alphanumeric data that indicates a proper and/or an optimal position of the transceiver 10A relative to the selected anatomical portion. Display 24 may be used to view two- or three-dimensional images of the selected anatomical region. Accordingly, the display 24 may be a liquid crystal display (LCD), a light emitting diode (LED) display, a cathode ray tube (CRT) display, or other suitable display devices operable to present alphanumeric data and/or graphical images to a user.

Still referring to FIG. 1A, a cavity selector 16 may be operable to adjustably adapt the transmission and reception of ultrasound signals to the anatomy of a selected patient. In particular, the cavity selector 16 adapts the transceiver 10A to accommodate various anatomical details of male and female patients. For example, when the cavity selector 16 is adjusted to accommodate a male patient, the transceiver 10A may be suitably configured to locate a single cavity, such as a urinary bladder in the male patient. In contrast, when the cavity selector 16 is adjusted to accommodate a female patient, the transceiver 10A may be configured to image an anatomical portion having multiple cavities, such as a bodily region that includes a bladder and a uterus. Alternate embodiments of the transceiver 10A may include a cavity selector 16 configured to select a single cavity scanning mode, or a multiple cavity-scanning mode that may be used with male and/or female patients. The cavity selector 16 may thus permit a single cavity region to be imaged, or a multiple cavity region, such as a region that includes a lung and a heart to be imaged.

To scan a selected anatomical portion of a patient, the transceiver dome 20 of the transceiver 10A may be positioned against a surface portion of a patient that is proximate to the anatomical portion to be scanned. The user actuates the transceiver 10A by depressing the trigger 14. In response, the transceiver 10 transmits ultrasound signals into the body, and receives corresponding return echo signals that may be at least partially processed by the transceiver 10A to generate an ultrasound image of the selected anatomical portion. In a particular embodiment, the transceiver 10A transmits ultrasound signals in a range that extends from approximately about two megahertz (MHz) to approximately about ten MHz.

In one embodiment, the transceiver 10A may be operably coupled to an ultrasound system that may be configured to generate ultrasound energy at a predetermined frequency and/or pulse repetition rate and to transfer the ultrasound energy to the transceiver 10A. The system also includes a processor that may be configured to process reflected ultrasound energy that is received by the transceiver 10A to produce an image of the scanned anatomical region. Accordingly, the system generally includes a viewing device, such as a cathode ray tube (CRT), a liquid crystal display (LCD), a plasma display device, or other similar display devices, that may be used to view the generated image. The system may also include one or more peripheral devices that cooperatively assist the processor to control the operation of the transceiver 10A, such a keyboard, a pointing device, or other similar devices. In still another particular embodiment, the transceiver 10A may be a self-contained device that includes a microprocessor positioned within the housing 18 and software associated with the microprocessor to operably control the transceiver 10A, and to process the reflected ultrasound energy to generate the ultrasound image. Accordingly, the display 24 may be used to display the generated image and/or to view other information associated with the operation of the transceiver 10A. For example, the information may include alphanumeric data that indicates a preferred position of the transceiver 10A prior to performing a series of scans. In yet another particular embodiment, the transceiver 10A may be operably coupled to a general-purpose computer, such as a laptop or a desktop computer that includes software that at least partially controls the operation of the transceiver 10A, and also includes software to process information transferred from the transceiver 10A, so that an image of the scanned anatomical region may be generated. The transceiver 10A may also be optionally equipped with electrical contacts to make communication with receiving cradles 50 as discussed in FIGS. 3 and 4 below. Although transceiver 10A of FIG. 1A may be used in any of the foregoing embodiments, other transceivers may also be used. For example, the transceiver may lack one or more features of the transceiver 10A. For example, a suitable transceiver need not be a manually portable device, and/or need not have a top-mounted display, and/or may selectively lack other features or exhibit further differences.

Referring still to FIG. 1A is a graphical representation of a plurality of scan planes that form a three-dimensional (3D) array having a substantially conical shape. An ultrasound scan cone 40 formed by a rotational array of two-dimensional scan planes 42 projects outwardly from the dome 20 of the transceivers 10A. The other transceiver embodiments 10B-10E may also be configured to develop a scan cone 40 formed by a rotational array of two-dimensional scan planes 42. The pluralities of scan planes 40 may be oriented about an axis 11 extending through the transceivers 10A-10E. One or more, or preferably each of the scan planes 42 may be positioned about the axis 11, preferably, but not necessarily at a predetermined angular position $\theta$. The scan planes 42 may be mutually spaced apart by angles $\theta_1$ and $\theta_2$. Correspondingly, the scan lines within each of the scan planes 42 may be spaced apart by angles $\phi_1$ and $\phi_2$. Although the angles $\theta_1$ and $\theta_2$ are depicted as approximately equal, it is understood that the angles $\theta_1$ and $\theta_2$ may have different values. Similarly, although the angles $\phi_1$ and $\phi_2$ are shown as approximately equal, the angles $\phi_1$ and $\phi_2$ may also have different angles. Other scan cone configurations are possible. For example, a wedge-shaped scan cone, or other similar shapes may be generated by the transceiver 10A, 10B and 10C.

FIG. 1B is a graphical representation of a scan plane 42. The scan plane 42 includes the peripheral scan lines 44 and 46, and an internal scan line 48 having a length r that extends outwardly from the transceivers 10A-10E. Thus, a selected point along the peripheral scan lines 44 and 46 and the internal scan line 48 may be defined with reference to the distance r and angular coordinate values $\phi$ and $\theta$. The length r preferably extends to approximately 18 to 20 centimeters (cm), although any length is possible. Particular embodiments include approximately seventy-seven scan lines 48 that extend outwardly from the dome 20, although any number of scan lines is possible.

FIG. 1C a graphical representation of a plurality of scan lines emanating from a hand-held ultrasound transceiver forming a single scan plane 42 extending through a cross-section of an internal bodily organ. The number and location of the internal scan lines emanating from the transceivers 10A-10E within a given scan plane 42 may thus be distributed at different positional coordinates about the axis line 11 as required to sufficiently visualize structures or images within the scan plane 42. As shown, four portions of an off-centered region-of-interest (ROI) are exhibited as irregular regions 49. Three portions may be viewable within the scan plane 42 in totality, and one may be truncated by the peripheral scan line 44.

As described above, the angular movement of the transducer may be mechanically effected and/or it may be electronically or otherwise generated. In either case, the number of lines 48 and the length of the lines may vary, so that the tilt angle $\theta$ sweeps through angles approximately between −60° and +60° for a total arc of approximately 120°. In one particular embodiment, the transceiver 10 may be configured to generate approximately about seventy-seven scan lines between the first limiting scan line 44 and a second limiting scan line 46. In another particular embodiment, each of the scan lines has a length of approximately about 18 to 20 centimeters (cm). The angular separation between adjacent scan lines 48 (FIG. 1B) may be uniform or non-uniform. For example, and in another particular embodiment, the angular separation $\phi_1$ and $\phi_2$ (as shown in FIG. 5C) may be about 1.5°. Alternately, and in another particular embodiment, the angular separation $\phi_1$ and $\phi_2$ may be a sequence wherein adjacent angles may be ordered to include angles of 1.5°, 6.8°, 15.5°, 7.2°, and so on, where a 1.5° separation is between a first scan line and a second scan line, a 6.8° separation is between the second scan line and a third scan line, a 15.5° separation is between the third scan line and a fourth scan line, a 7.2° separation is between the fourth scan line and a fifth scan line, and so on. The angular separation between adjacent scan lines may also be a combination of uniform and non-uniform angular spacings, for example, a sequence of angles may be ordered to include 1.5°, 1.5°, 1.5°, 7.2°, 14.3°, 20.2°, 8.0°, 8.0°, 8.0°, 4.3°, 7.8°, and so on.

FIG. 1D is an isometric view of an ultrasound scan cone that projects outwardly from the transceivers of FIGS. 1A-E. Three-dimensional images of a region of interest may be presented within a scan cone 40 that comprises a plurality of 2D images formed in an array of scan planes 42. A dome cutout 41 that is the complementary to the dome 20 of the transceivers 10A-10E is shown at the top of the scan cone 40.

Figure 2:
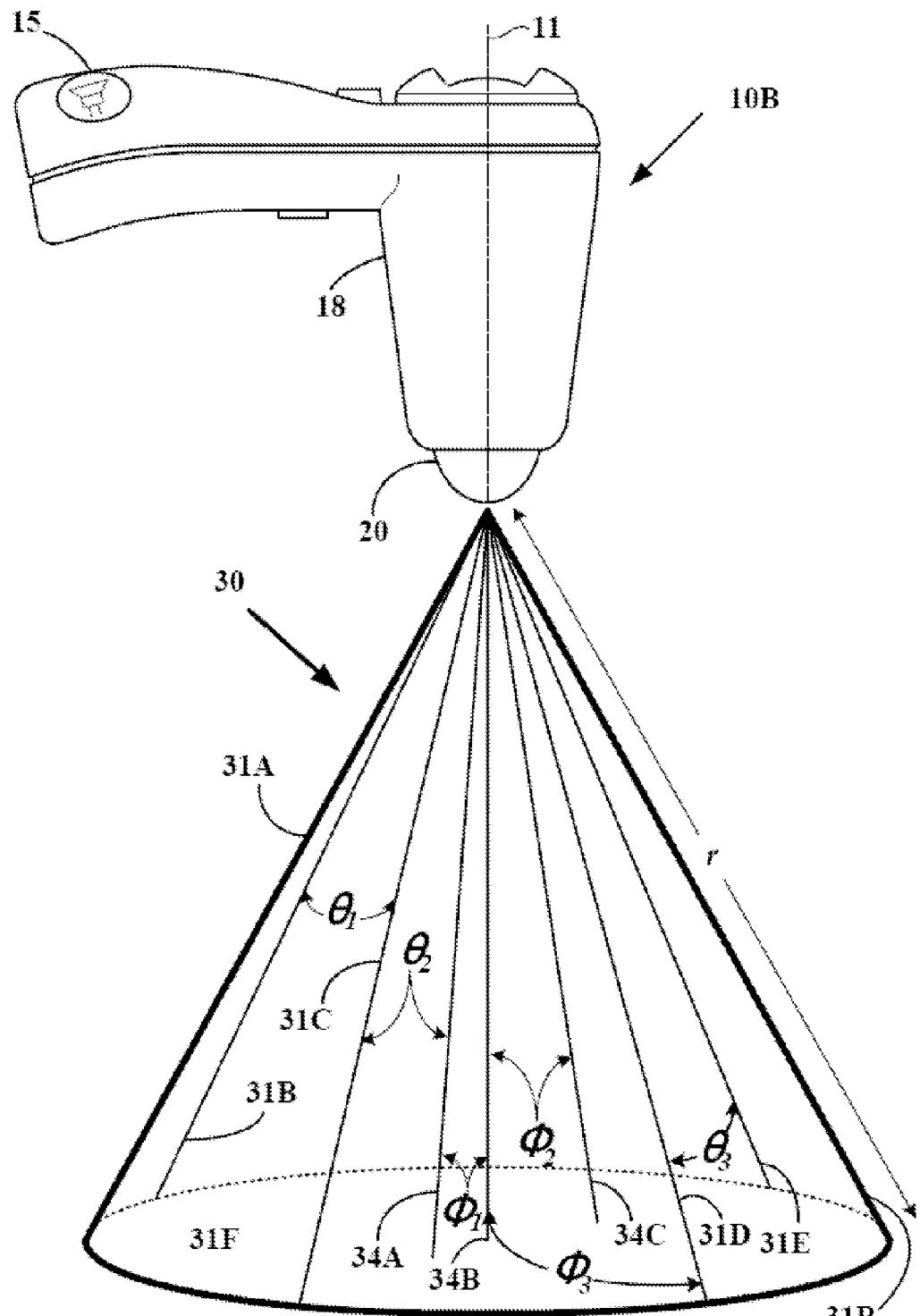
FIG. 2 depicts a partial schematic and partial isometric and side view of a transceiver, and a scan cone array comprised of 3D-distributed scan lines in alternate embodiment of an ultrasound harmonic imaging system.

FIG. 2 depicts a partial schematic and partial isometric and side view of a transceiver, and a scan cone array comprised of 3D-distributed scan lines in alternate embodiment of an ultrasound harmonic imaging system. A plurality of three-dimensional (3D) distributed scan lines emanating from a transceiver that cooperatively forms a scan cone 30. Each of the scan lines have a length r that projects outwardly from the transceivers 10A-10E of FIGS. 1A-1E. As illustrated the transceiver 10A emits 3D-distributed scan lines within the scan cone 30 that may be one-dimensional ultrasound A-lines. The other transceiver embodiments 10B-10E may also be configured to emit 3D-distributed scan lines. Taken as an aggregate, these 3D-distributed A-lines define the conical shape of the scan cone 30. The ultrasound scan cone 30 extends outwardly from the dome 20 of the transceiver 10A, 10B and 10C centered about an axis line 11. The 3D-distributed scan lines of the scan cone 30 include a plurality of internal and peripheral scan lines that may be distributed within a volume defined by a perimeter of the scan cone 30. Accordingly, the peripheral scan lines 31A-31F define an outer surface of the scan cone 30, while the internal scan lines 34A-34C may be distributed between the respective peripheral scan lines 31A-31F. Scan line 34B may be generally collinear with the axis 11, and the scan cone 30 may be generally and coaxially centered on the axis line 11.

The locations of the internal and peripheral scan lines may be further defined by an angular spacing from the center scan line 34B and between internal and peripheral scan lines. The angular spacing between scan line 34B and peripheral or internal scan lines may be designated by angle $\Phi$ and angular spacings between internal or peripheral scan lines may be designated by angle Ø. The angles $\Phi_1$, $\Phi_2$, and $\Phi_3$ respectively define the angular spacings from scan line 34B to scan lines 34A, 34C, and 31D. Similarly, angles $Ø_1$, $Ø_2$, and $Ø_3$ respectively define the angular spacings between scan line 31B and 31C, 31C and 34A, and 31D and 31E.

With continued reference to FIG. 2, the plurality of peripheral scan lines 31A-E and the plurality of internal scan lines 34A-D may be three dimensionally distributed A-lines (scan lines) that are not necessarily confined within a scan plane, but instead may sweep throughout the internal regions and along the periphery of the scan cone 30. Thus, a given point within the scan cone 30 may be identified by the coordinates r, $\Phi$, and Ø whose values generally vary. The number and location of the internal scan lines emanating from the transceivers 10A-10E may thus be distributed within the scan cone 30 at different positional coordinates as required to sufficiently visualize structures or images within a region of interest (ROI) in a patient. The angular movement of the ultrasound transducer within the transceiver 10A-10E may be mechanically effected, and/or it may be electronically generated. In any case, the number of lines and the length of the lines may be uniform or otherwise vary, so that angle $\Phi$ sweeps through angles approximately between −60° between scan line 34B and 31A, and +60° between scan line 34B and 31B. Thus angle $\Phi$ in this example presents a total arc of approximately 120°. In one embodiment, the transceiver 10A, 10B and 10C may be configured to generate a plurality of 3D-distributed scan lines within the scan cone 30 having a length r of approximately 18 to 20 centimeters (cm).

Figure 3:
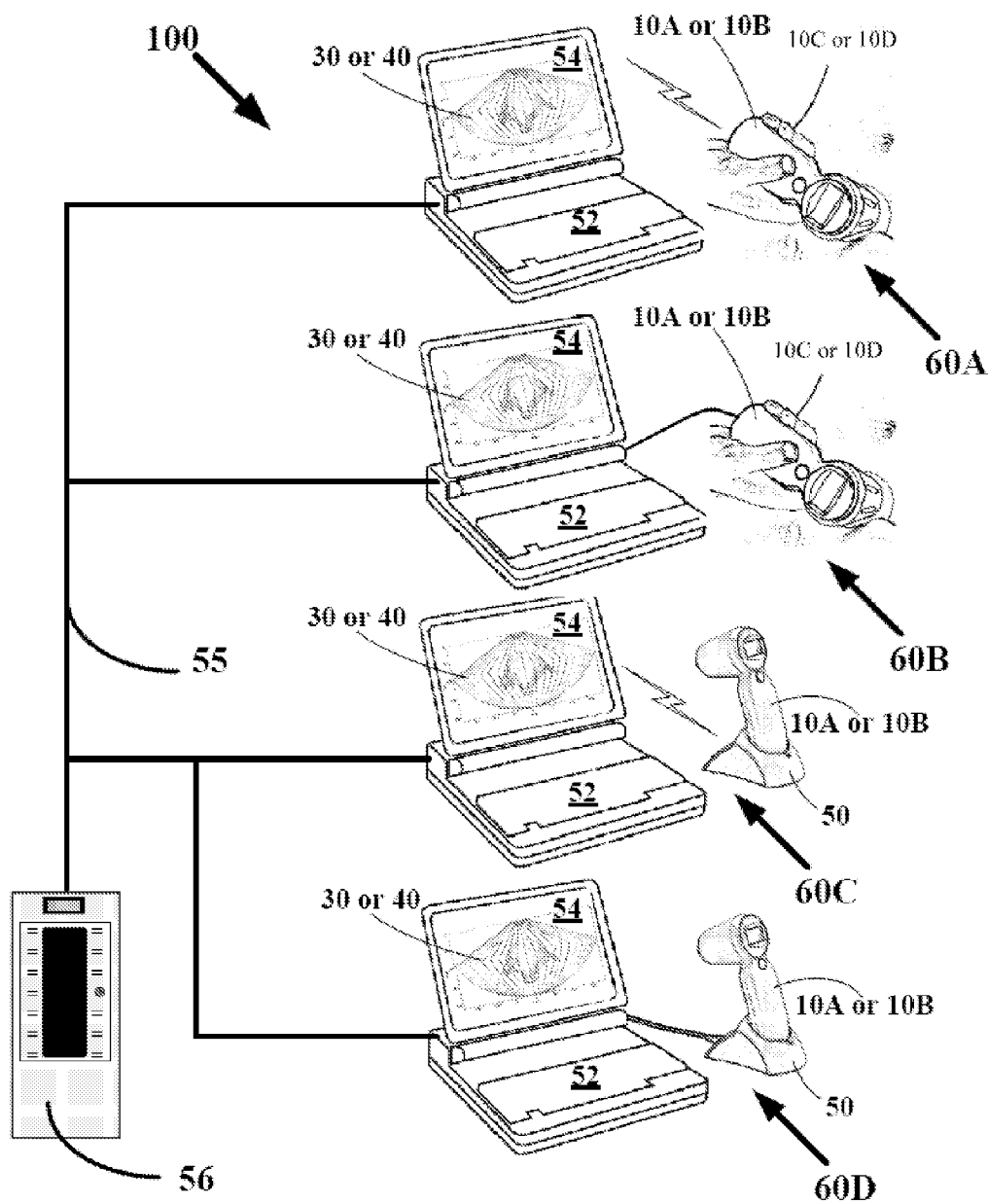
FIG. 3 is a schematic illustration of a server-accessed local area network in communication with a plurality of ultrasound harmonic imaging systems.

FIG. 3 is a schematic illustration of a server-accessed local area network in communication with a plurality of ultrasound harmonic imaging systems. An ultrasound harmonic imaging system 100 includes one or more personal computer devices 52 that may be coupled to a server 56 by a communications system 55. The devices 52 may be, in turn, coupled to one or more ultrasound transceivers 10A and/or 10B, for examples the ultrasound harmonic sub-systems 60A-60D. Ultrasound based images of organs or other regions of interest derived from either the signals of echoes from fundamental frequency ultrasound and/or harmonics thereof, may be shown within scan cone 30 or 40 presented on display 54. The server 56 may be operable to provide additional processing of ultrasound information, or it may be coupled to still other servers (not shown in FIG. 3) and devices. Transceivers 10A or 10B may be in wireless communication with computer 52 in sub-system 60A, in wired signal communication in sub-system 10B, in wireless communication with computer 52 via receiving cradle 50 in sub-system 10C, or in wired communication with computer 52 via receiving cradle 50 in sub-system 10D.

Figure 4:
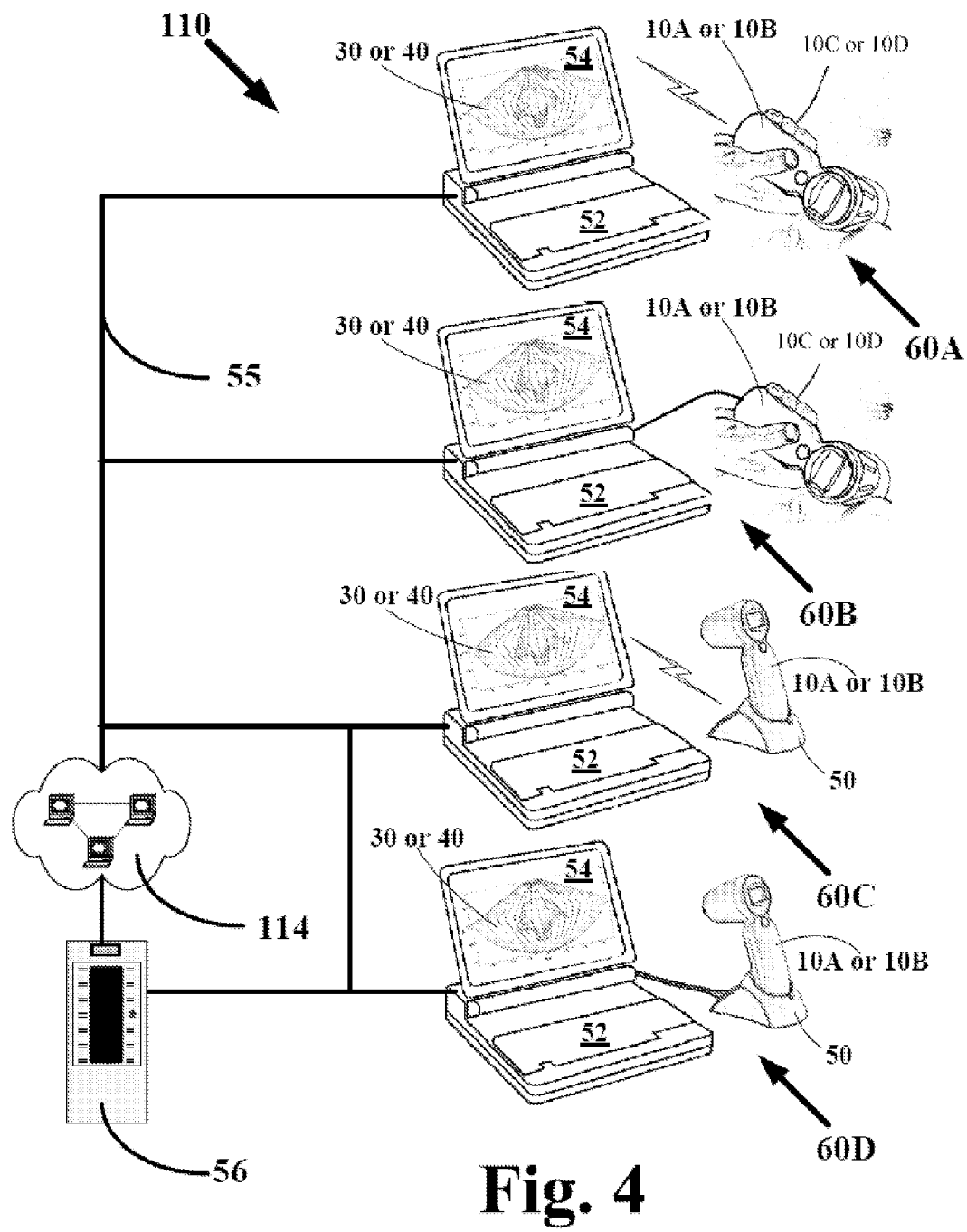
FIG. 4 is a schematic illustration of the Internet in communication with a plurality of ultrasound harmonic imaging systems.

FIG. 4 is a schematic illustration of the Internet in communication with a plurality of ultrasound harmonic imaging systems. An Internet system 110 may be coupled or otherwise in communication with the ultrasound harmonic sub-systems 60A-60D.

Figure 5:
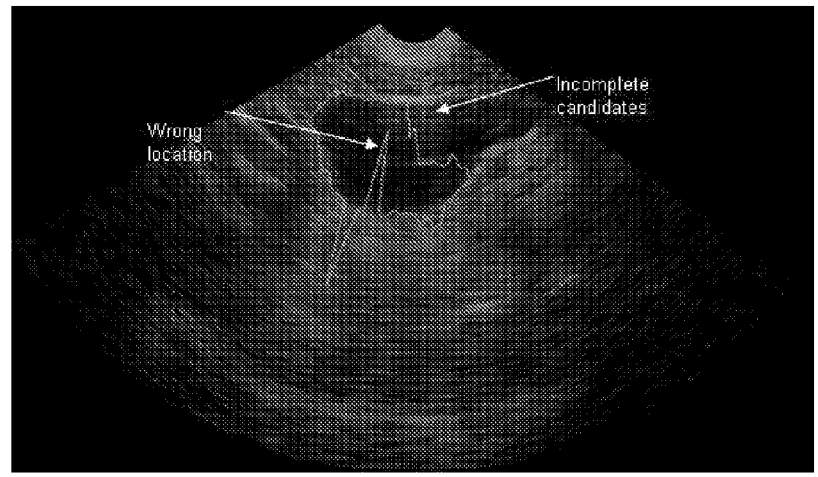
FIG. 5 illustrates an improperly segmented bladder determined by echo histogram intensity along 1D scan lines.

FIG. 5 illustrates a Cartesian presented scan plane having an improperly segmented bladder determined by echo histogram intensity along 1D scan lines. One-dimensional scan lines cannot fully use image information available in 2D with the result that a segmented bladder is prone underestimation and/or overestimation due to improper segmentation. Here a large portion of the bladder is missed due to the selection of incomplete pixel candidates in the bladder lumen, and incomplete pixel wall candidates outside the bladder region gives overestimation. The cavity border diction in this image was not correctable utilizing pattern recognition algorithms using a support vector machine (SVM). Moreover, pattern recognition requires training, and if the cavity shapes substantially vary from that shape used in training, for example from a substantially spherical (ball like, grapefruit or melon like) to a substantially tubular or cylindrical configuration, segmentation will be inaccurate. SVM is not able to neither extract the missing pixels nor utilize all the 2D image information.

Figure 6:
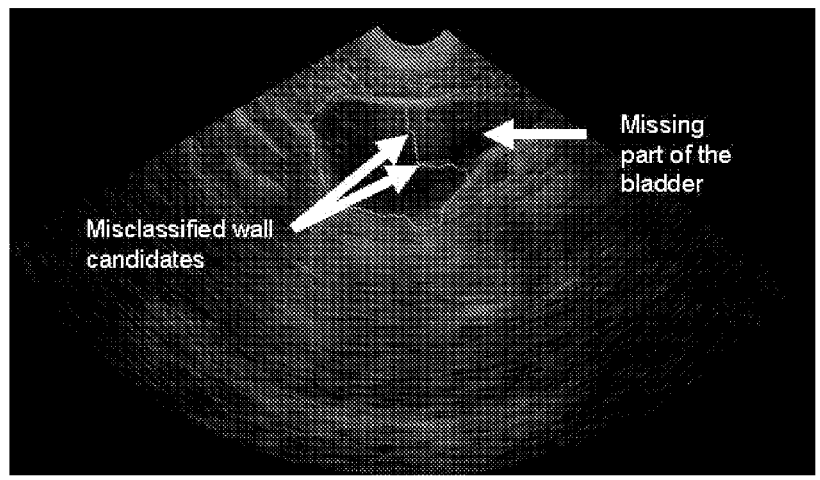
FIG. 6 illustrates an example of an improperly segmented bladder under 2D scan plane algorithms dependent on pattern recognition.

FIG. 6 illustrates a Cartesian presented scan plane example of an improperly segmented bladder under 2D scan plane algorithms using a live wire algorithm to link available pixel candidate wall boundary points.

Figure 7:
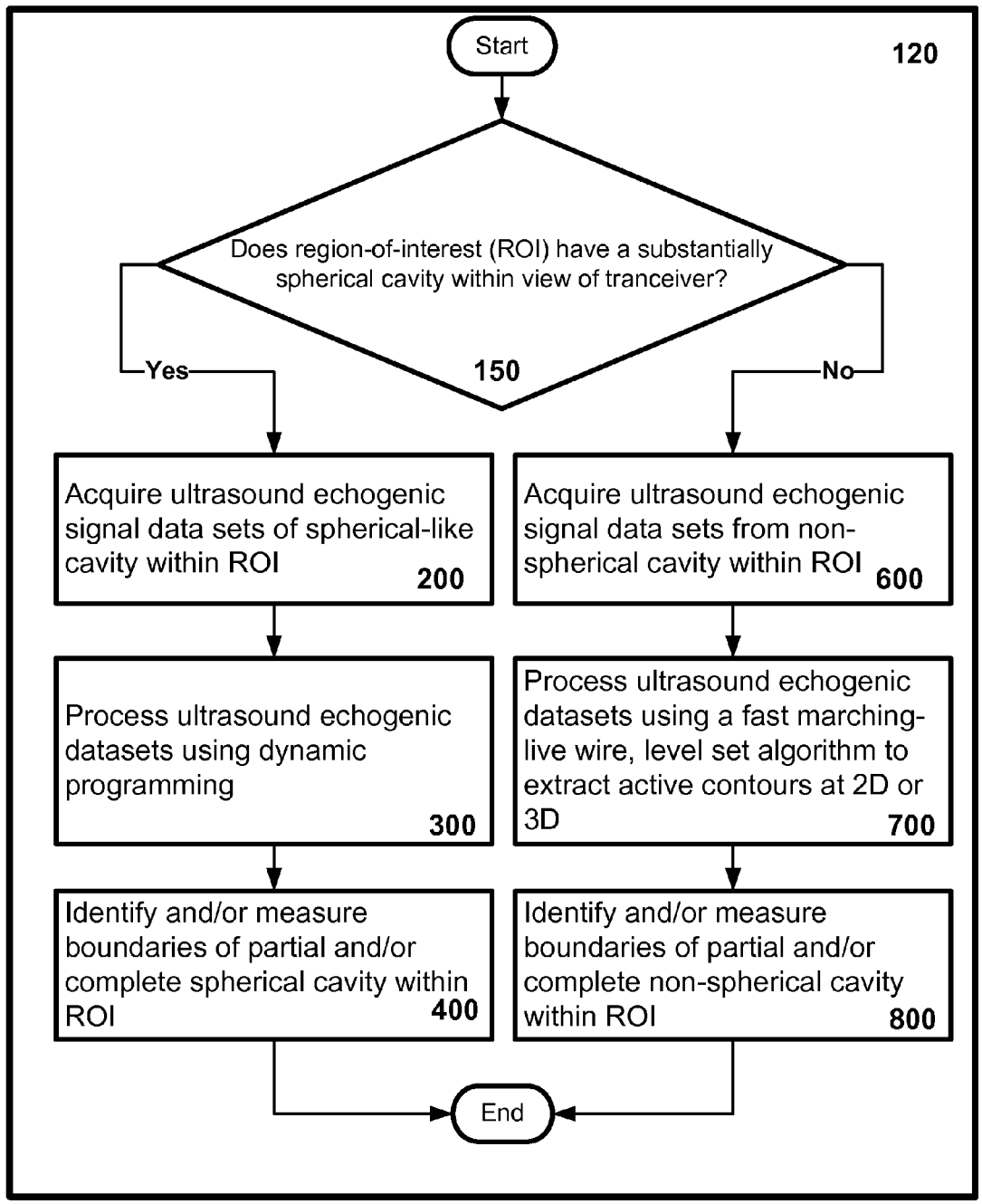
FIG. 7 schematically depicts a method flow chart algorithm 120 of shape-driven live wire algorithms to acquire, identify, and measure the boundaries of an organ.

FIG. 7 schematically depicts a method flow chart for master algorithm 120 to acquire, identify, and measure the boundaries of a cavity surrounded by and/or adjacent to echogenic tissue. Master algorithm 120 begins with decision diamond 150 with a query "Does region-of-interest (ROI) have a substantially spherical cavity within view of transceiver?". Substantially spherical cavity doesn't require an exact ball shaped cavity, but may include an uneven spherical shape, for example, an oval like grapefruit shape, or other asymmetrical or slightly lopsided spherical shape. Master algorithm 120 presents an affirmative branch or "Yes" response processing block column and a negative branch or "No" response processing block column to the query.

If affirmative for a substantially spherical cavity, master algorithm 120 continues with process block 200 wherein ultrasound echogenic signal data sets are acquired for the spherical-like cavity within the ROI. Thereafter, at process block 300, a dynamic programming method processes the signal data sets acquired for the spherical-like cavity to determine the contour along the cavity-tissue boundary interface. Then, at processing block 400, the contour of the cavity-tissue boundary interface is identified and/or measured. Master algorithm 120 then is completed along the affirmative branch.

If negative for a substantially spherical cavity, master algorithm 120 continues with process block 600 wherein ultrasound echogenic signal data sets are acquired for a non spherical-like cavity within the ROI. Non-spherical cavities include column or tube-like cavities, for example, cavities broadly defining for arteries, veins, and lymph vessels. The column-like vessels may be in substantially linear section of the vessels, and/or the twisting and turning portions of vessels. Thereafter, at process block 700, a fast marching-live wire algorithm (2D) or level set active contour method (2D or 3D) processes the tube-like signal data sets to determine the contour along the column cavity-tissue boundary interface. Then, at processing block 800, the contour of the tube-like or non-spherical cavity-tissue boundary interface is identified and/or measured. Master algorithm 120 then is completed along the negative or non-spherical branch.

Figure 8:
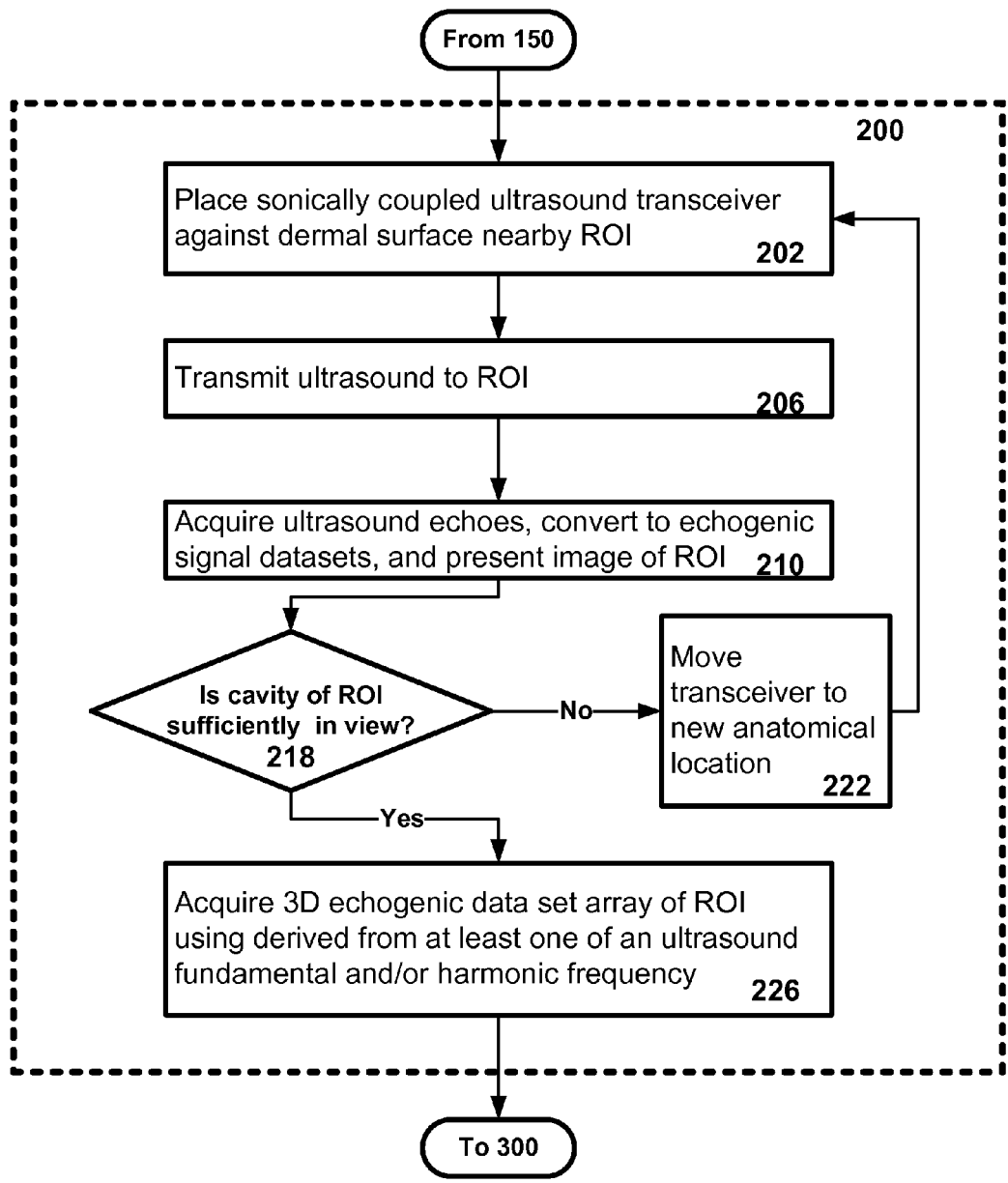
FIG. 8 is an expansion of sub-algorithm 200 of master algorithm 120 of FIG. 7.

FIG. 8 is an expansion of sub-algorithm 200 of master algorithm 120 of FIG. 7 concerning acquisition echogenic signal data sets of spherical like cavities. Sub-algorithms 200 begin with applying placing the transceiver 10A or 10B firmly against the dermal surface of a subject that is nearby the ROI. By "nearby" is meant that at least a portion of a spherical-like or tube-like cavity is visible on either the transceiver's 10A's or 10B's display 16, and/or computer display 54. Thereafter, at process block 206, radio-frequency ultrasound is transmitted to the ROI having spherical-like and/or column-like cavities. Following at process block 210, ultrasound echoes returning from the ROI are acquired by the transceivers and converted to signals, and the signals are presented as echogenic datasets on the transceiver display 16 and/or computer display 54. Thereafter, at decision diamond 218, a query is presented "Is cavity of ROI sufficiently in view?", and if affirmative, i.e., sufficiently in view, for example the cavity is centered or otherwise discernable to acquire a 3D dataset, sub-algorithm 200A,B continues and is completed at process block 226 for acquisition of a 3D echogenic data set scanplane substantially similar to scan cone 40 of FIG. 1A or scan cone 30 of FIG. 2. The 3D echogenic data set may be derived from the fundamental ultrasound frequency or harmonic thereof. If the answer is negative for sufficiency for cavity presentation, then sub-algorithm 200A,B resumes to process block 222 in which the transceiver 10A or 10B is moved to a new anatomical location, i.e., a new dermal surface location, for reacquisition of a spherical-like or tube-like cavity image at process block 202. The image reacquisition loop from process blocks 202 through 222 is repeated until an affirmative cavity image is acquired for completion at process block 226. The 3D datasets may be formed from echoes derived from the probing fundamental ultrasound frequency, or any harmonic thereof. Sub-algorithm 200 is completed and exits to sub-algorithm 300.

Figure 9:
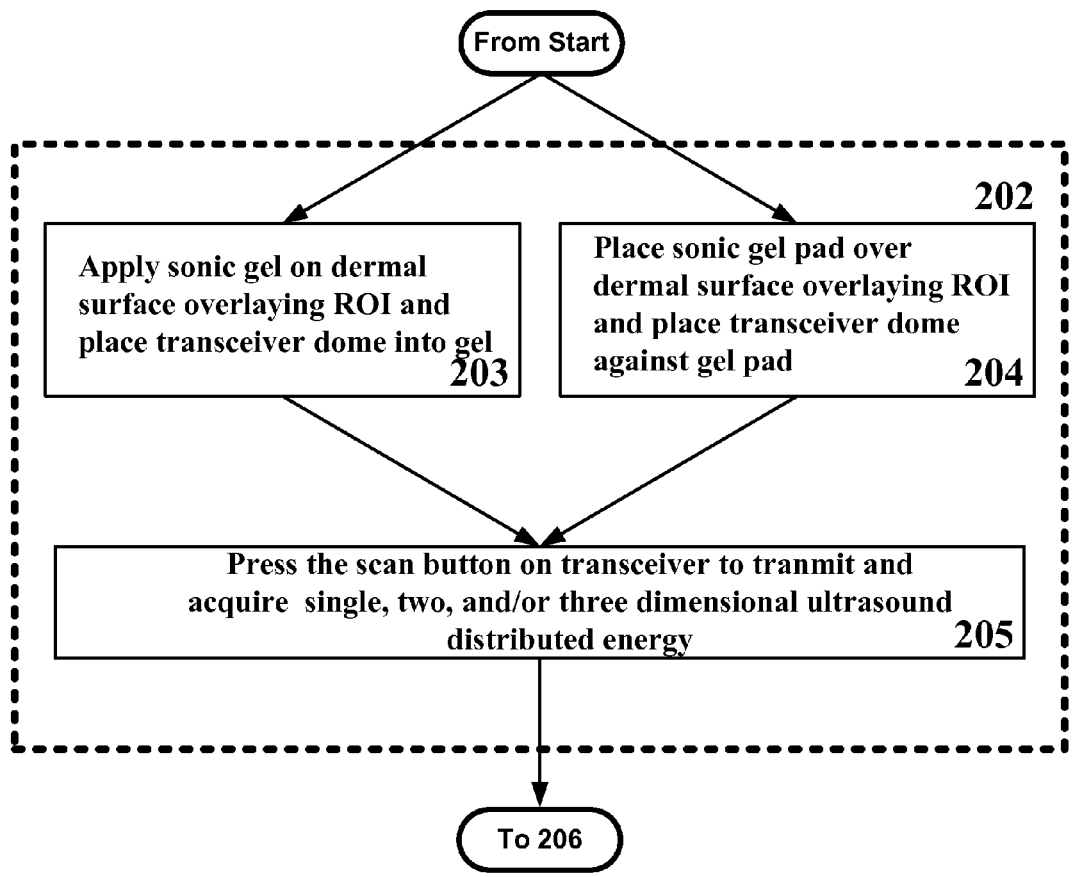
FIG. 9 is an expansion of sub-algorithms 202 of FIG. 8.

FIG. 9 is an expansion of sub-algorithms 202 of FIG. 8 for securing a good sonic coupling from the transceiver 10A,B against the dermal surface of the subject. At process block 203, a sonic gel is applied against the dermal surface overlaying the ROI and the transceiver dome 20 is placed into the gel so that a firm sonic coupling from transceiver 10A,B is established so that efficient transmission of ultrasound energy is conveyed. Alternatively, at process block 205, a pad containing sonic gel is placed against the dermal surface and the transceiver dome 20 is firmly pressed against the sonic gel pad so that efficient transfer of ultrasound energy is possible. Thereafter, at process block 205, ultrasound energy is transmitted and received that may be in the form of single dimensional scan lines similar to scanlines 44,48 of FIG. 1D, two-dimensional distributed ultrasound similar to scan planes 42 of FIGS. 1B-D, and/or three-dimensional distributed ultrasound similar to the rotational scan plane array of scancone 40 of FIG. 1B, and/or 3D distributed scanlines similar to scan cone 30 of FIG. 2. Thereafter sub-algorithm 202 is completed and exits to sub-algorithm 206.

Figure 10:
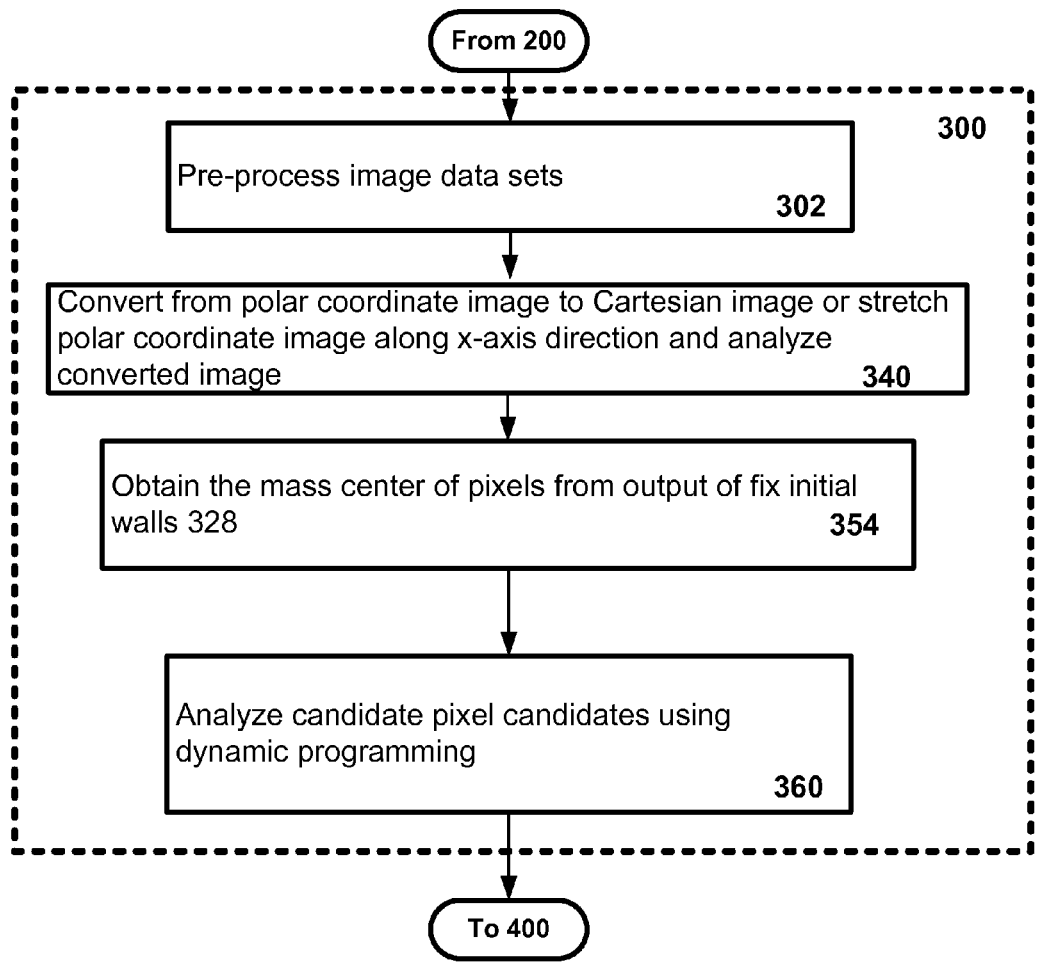
FIG. 10 is an expansion of sub-algorithm 300 of master algorithm illustrated in FIG. 7.
Figure 28:
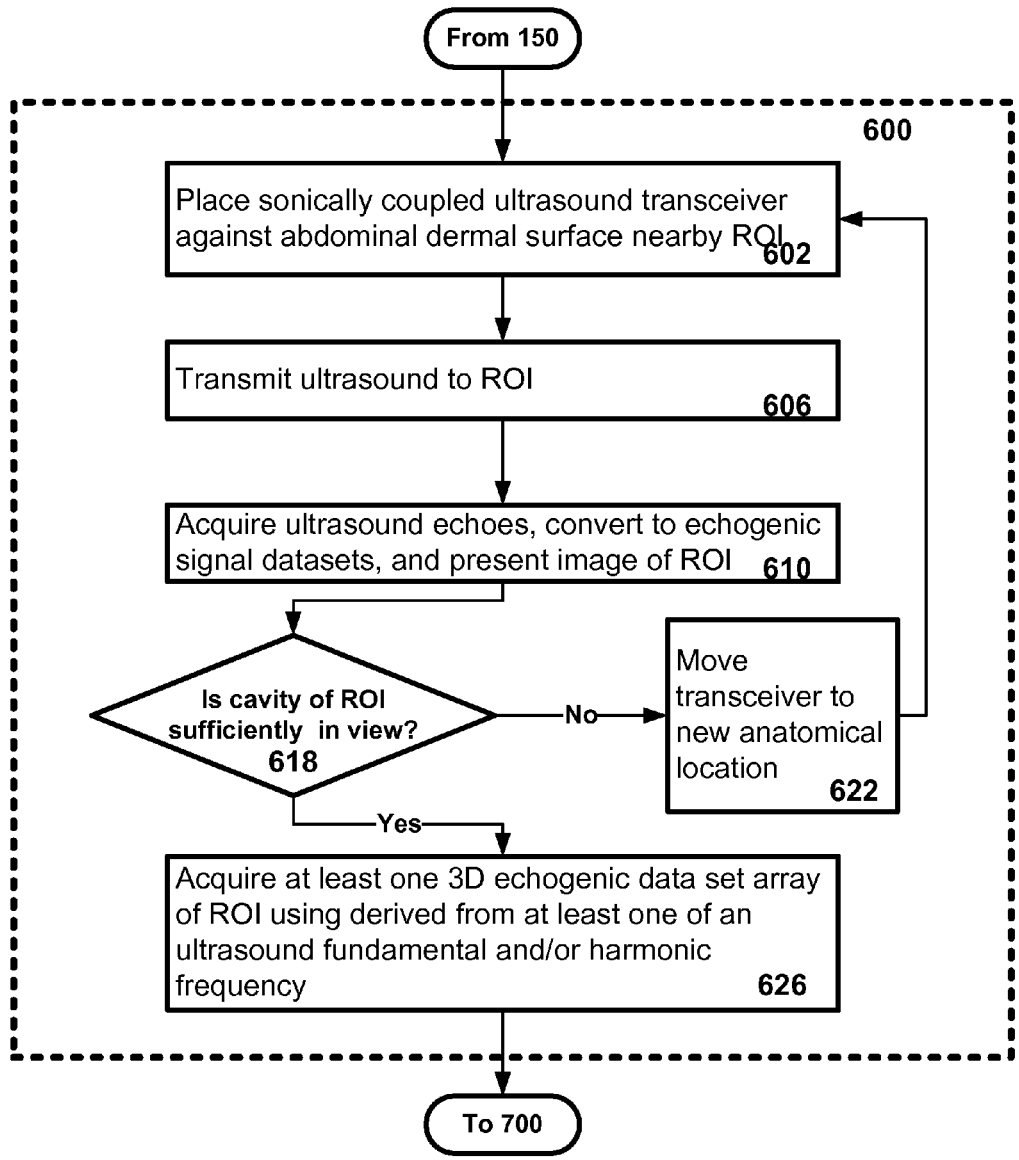
FIG. 28 is an expansion of sub-algorithm 600 of master algorithm 120 of FIG. 7.
Figure 29:
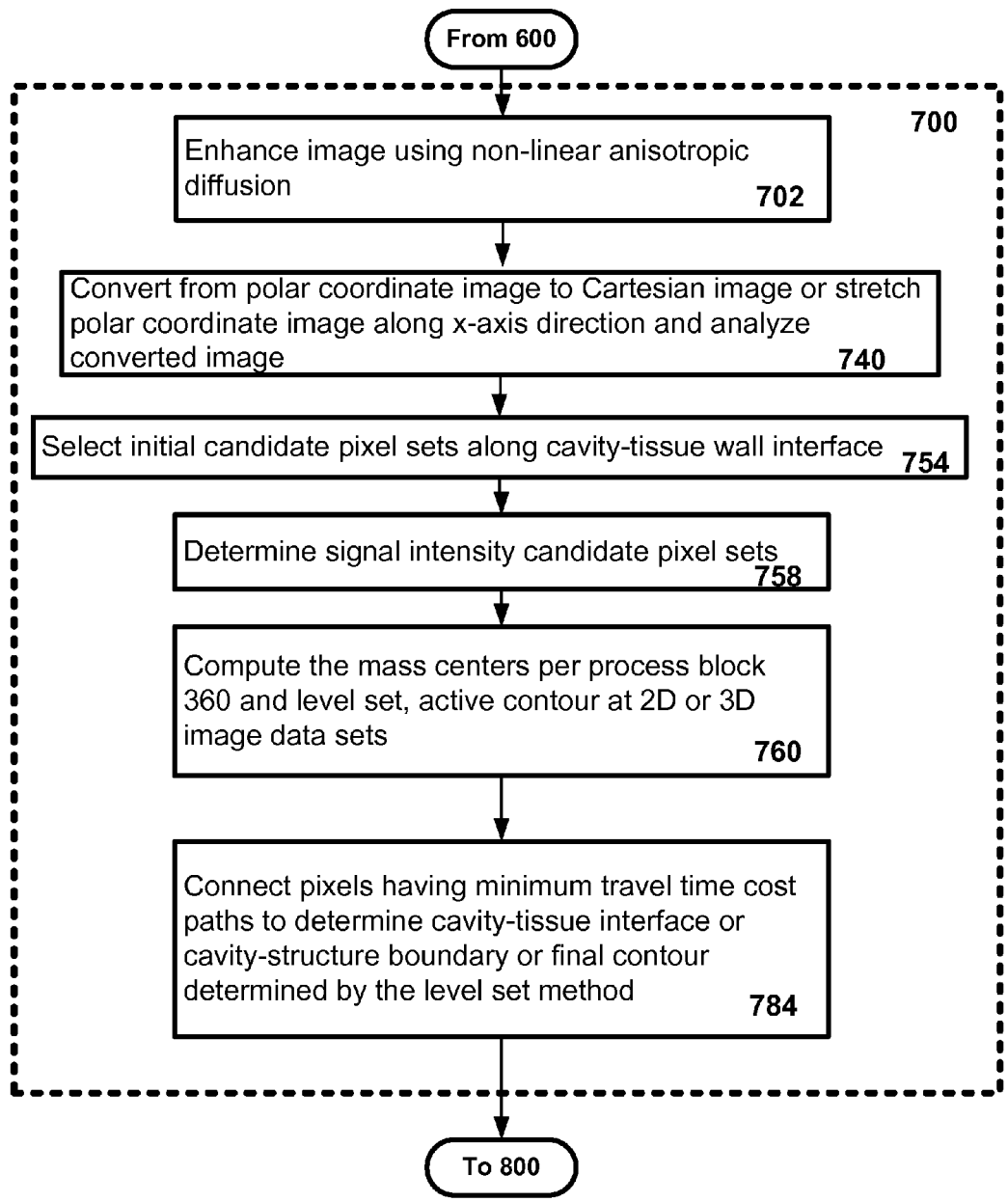
FIG. 29 is an expansion of sub-algorithm 700.

FIG. 10 is an expansion of sub-algorithm 300 concerning the dymanic programming processing of echogenic signals of master algorithm 120 illustrated in FIG. 7. From sub-algorithm 200, sub-algorithm 300 begins with pre-processing of echogenic signals of image data sets at process block 302, more fully described in FIG. 11 below. After signal pre-processing, initially acquired polar coordinate 2D ultrasound images are converted to either a Cartesian format, or stretched in the X-axis direction in process block 340 so that roundness may be conferred to the teardrop shaped polar coordinate images more amenable for segmentation by the fast marching-live wire algorithm. The conversion to Cartesian or X-axis stretched 2D images are illustrated in FIGS. 21 and 28-29 below. Transformation to Cartesian coordinates may be achieved using Matlab® from MathWorks Inc., Natick, Mass., USA, herein incorporated by reference, using the command file polarstretch.m. Thereafter, a seed point is selected using the bladder walls computed in blocks 354 and 358.

Figure 11:
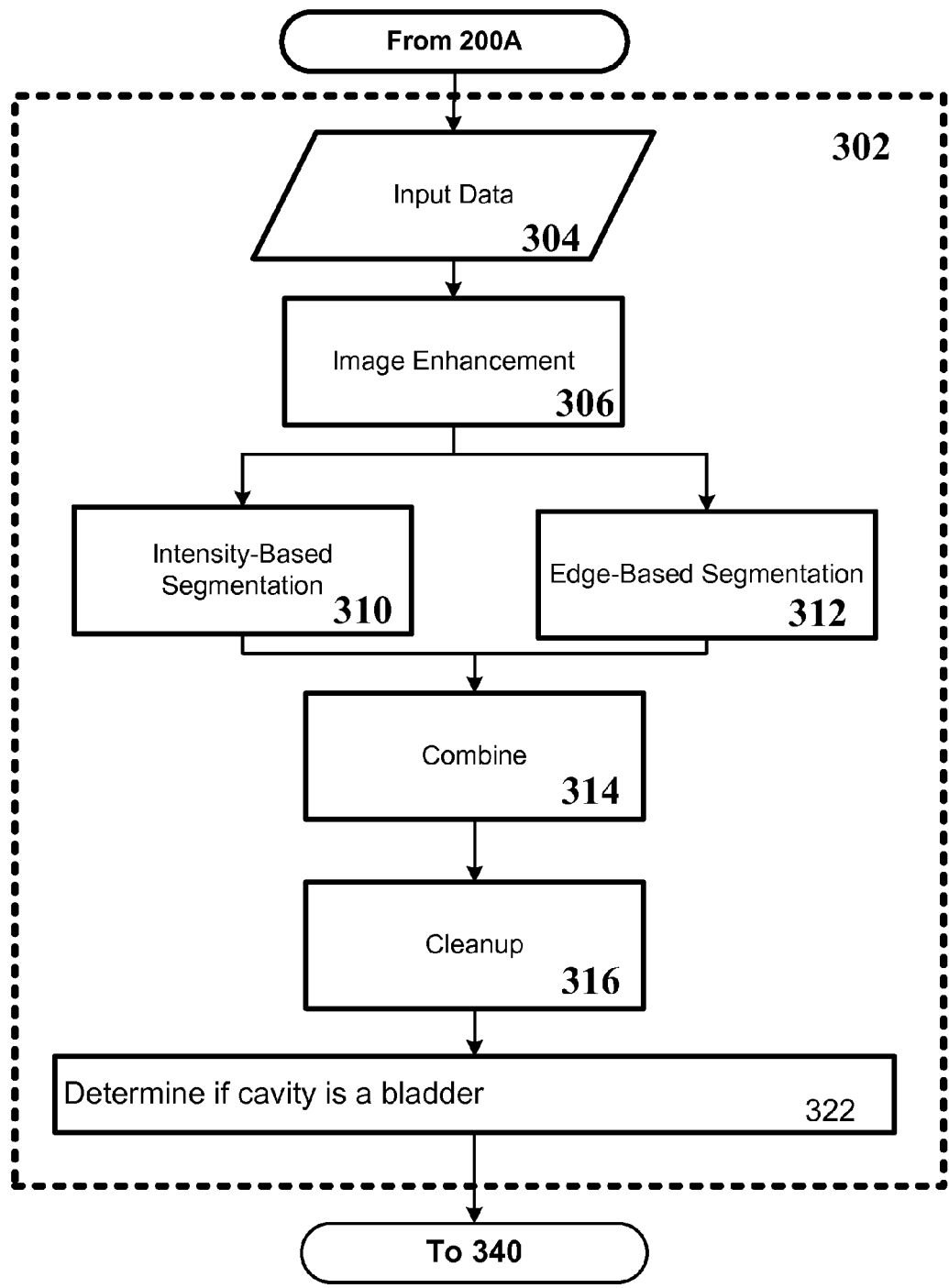
FIG. 11 is an expansion of sub-algorithm 302 of FIG. 10.

FIG. 11 is an expansion of sub-algorithm 302 of FIG. 10. 3D data sets are entered at input data process block 304 that then undergoes a 2-step image enhancement procedure at process block 306. The 2-step image enhancement includes performing a heat filter to reduce noise followed by a shock filter to sharpen edges of structures within the 3D data sets. The heat and shock filters are partial differential equations (PDE) defined respectively in Equations E1 and E2 below:

$$E1: \frac{\partial u}{\partial t} = \frac{\partial^2 u}{\partial x^2} + \frac{\partial^2 u}{\partial y^2} \quad \text{(Heat Filter)}$$

$$E2: \frac{\partial u}{\partial t} = -F(\ell(u)) \|\nabla u\| \quad \text{(Shock Filter)}$$

Here u in the heat filter represents the image being processed. The image u is 2D, and is comprised of an array of pixels arranged in rows along the x-axis, and an array of pixels arranged in columns along the y-axis. The pixel intensity of each pixel in the image u has an initial input image pixel intensity (I) defined as $u_0$=I. The value of I depends on the application, and commonly occurs within ranges consistent with the application. For example, I can be as low as 0 to 1, or occupy middle ranges between 0 to 127 or 0 to 512. Similarly, I may have values occupying higher ranges of 0 to 1024 and 0 to 4096, or greater. For the shock filter u represents the image being processed whose initial value is the input image pixel intensity (I): $u_0$=I where the l(u) term is the Laplacian of the image u, F is a function of the Laplacian, and is the 2D gradient magnitude of image intensity defined by equation E3:

$$\|\nabla u\| = \sqrt{u_x^2 + u_y^2} \qquad \text{E3}$$

Where $u^2_x$=the square of the partial derivative of the pixel intensity (u) along the x-axis, $u^2_y$=the square of the partial derivative of the pixel intensity (u) along the y-axis, the Laplacian l(u) of the image, u, is expressed in equation E4:

$$l(u) = u_{xx}u_x^2 + 2u_{xy}u_x u_y + u_{yy}u_y^2 \qquad \text{E4}$$

Equation E9 relates to equation E6 as follows:

$u_x$ is the first partial derivative $$\frac{\partial u}{\partial x}$$

of u along the x-axis, $u_x u_y$ is the first partial derivative $$\frac{\partial u}{\partial y}$$

of u along the y-axis, $u_x u_x^2$ is the square of the first partial derivative $$\frac{\partial u}{\partial x}$$

of u along the x-axis, $u_x u_y^2$ is the square of the first partial derivative $$\frac{\partial u}{\partial y}$$

of u along the y-axis, $U_x u_{xx}$ is the second partial derivative $$\frac{\partial^2 u}{\partial x^2}$$

of u along the x-axis, $u_x u_{yy}$ is the second partial derivative $$\frac{\partial^2 u}{\partial y^2}$$

of u along the y-axis, $u_{xy}$ is cross multiple first partial derivative $$\frac{\partial u}{\partial x \partial y}$$

of u along the x and y axes, and $u_{xy}$ the sign of the function F modifies the Laplacian by the image gradient values selected to avoid placing spurious edges at points with small gradient values:

$$F(\ell(u)) = 1, \text{ if } \ell(u) > 0 \text{ and } \|\nabla u\| > t$$
$$= -1, \text{ if } \ell(u) < 0 \text{ and } \|\nabla u\| > t$$
$$= 0, \text{ otherwise}$$

where t is a threshold on the pixel gradient value $\|\nabla u\|$.

The combination of heat filtering and shock filtering produces an enhanced image ready to undergo the intensity-based and edge-based segmentation algorithms as discussed below. The enhanced 3D data sets are then subjected to a parallel process of intensity-based segmentation at process block 310 and edge-based segmentation at process block 312. The intensity-based segmentation step uses a "k-means" intensity clustering technique where the enhanced image is subjected to a categorizing "k-means" clustering algorithm. The "k-means" algorithm categorizes pixel intensities into white, gray, and black pixel groups. Given the number of desired clusters or groups of intensities (k), the k-means algorithm is an iterative algorithm comprising four steps: Initially determine or categorize cluster boundaries by defining a minimum and a maximum pixel intensity value for every white, gray, or black pixels into groups or k-clusters that are equally spaced in the entire intensity range. Assign each pixel to one of the white, gray or black k-clusters based on the currently set cluster boundaries. Calculate a mean intensity for each pixel intensity k-cluster or group based on the current assignment of pixels into the different k-clusters. The calculated mean intensity is defined as a cluster center. Thereafter, new cluster boundaries are determined as mid points between cluster centers. The fourth and final step of intensity-based segmentation determines if the cluster boundaries significantly change locations from their previous values. Should the cluster boundaries change significantly from their previous values, iterate back to step 2, until the cluster centers do not change significantly between iterations. Visually, the clustering process is manifest by the segmented image and repeated iterations continue until the segmented image does not change between the iterations.

The pixels in the cluster having the lowest intensity value—the darkest cluster—are defined as pixels associated with internal cavity regions of bladders. For the 2D algorithm, each image is clustered independently of the neighboring images. For the 3D algorithm, the entire volume is clustered together. To make this step faster, pixels are sampled at 2 or any multiple sampling rate factors before determining the cluster boundaries. The cluster boundaries determined from the down-sampled data are then applied to the entire data.

The edge-based segmentation process block 312 uses a sequence of four sub-algorithms. The sequence includes a spatial gradients algorithm, a hysteresis threshold algorithm, a Region-of-Interest (ROI) algorithm, and a matching edges filter algorithm. The spatial gradient algorithm computes the x-directional and y-directional spatial gradients of the enhanced image. The hysteresis threshold algorithm detects salient edges. Once the edges are detected, the regions defined by the edges are selected by a user employing the ROI algorithm to select regions-of-interest deemed relevant for analysis.

Since the enhanced image has very sharp transitions, the edge points can be easily determined by taking x- and y-derivatives using backward differences along x- and y-directions. The pixel gradient magnitude is $\|\nabla I\|$ then computed from the x- and y-derivative image in equation E5 as:

$$\|\nabla I\| = \sqrt{I_x^2 + I_y^2} \qquad \text{E5}$$

Where $I_x^2$=the square of x-derivative of intensity and $I_y^2$=the square of y-derivative of intensity along the y-axis.

Significant edge points are then determined by thresholding the gradient magnitudes using a hysteresis thresholding operation. Other thresholding methods could also be used. In hysteresis thresholding 530, two threshold values, a lower threshold and a higher threshold, are used. First, the image is thresholded at the lower threshold value and a connected component labeling is carried out on the resulting image. Next, each connected edge component is preserved which has at least one edge pixel having a gradient magnitude greater than the upper threshold. This kind of thresholding scheme is good at retaining long connected edges that have one or more high gradient points.

In the preferred embodiment, the two thresholds are automatically estimated. The upper gradient threshold is estimated at a value such that at most 97% of the image pixels are marked as non-edges. The lower threshold is set at 50% of the value of the upper threshold. These percentages could be different in different implementations. Next, edge points that lie within a desired region-of-interest are selected. This region of interest algorithm excludes points lying at the image boundaries and points lying too close to or too far from the transceivers 10A,B. Finally, the matching edge filter is applied to remove outlier edge points and fill in the area between the matching edge points.

The edge-matching algorithm is applied to establish valid boundary edges and remove spurious edges while filling the regions between boundary edges. Edge points on an image have a directional component indicating the direction of the gradient. Pixels in scanlines crossing a boundary edge location can exhibit two gradient transitions depending on the pixel intensity directionality. Each gradient transition is given a positive or negative value depending on the pixel intensity directionality. For example, if the scanline approaches an echo reflective bright wall from a darker region, then an ascending transition is established as the pixel intensity gradient increases to a maximum value, i.e., as the transition ascends from a dark region to a bright region. The ascending transition is given a positive numerical value. Similarly, as the scanline recedes from the echo reflective wall, a descending transition is established as the pixel intensity gradient decreases to or approaches a minimum value. The descending transition is given a negative numerical value.

Valid boundary edges are those that exhibit ascending and descending pixel intensity gradients, or equivalently, exhibit paired or matched positive and negative numerical values. The valid boundary edges are retained in the image. Spurious or invalid boundary edges do not exhibit paired ascending-descending pixel intensity gradients, i.e., do not exhibit paired or matched positive and negative numerical values. The spurious boundary edges are removed from the image.

For bladder cavity volumes, most edge points for blood fluid surround a dark, closed region, with directions pointing inwards towards the center of the region. Thus, for a convex-shaped region, the direction of a gradient for any edge point, the edge point having a gradient direction approximately opposite to the current point represents the matching edge point. Those edge points exhibiting an assigned positive and negative value are kept as valid edge points on the image because the negative value is paired with its positive value counterpart. Similarly, those edge point candidates having unmatched values, i.e., those edge point candidates not having a negative-positive value pair, are deemed not to be true or valid edge points and are discarded from the image.

The matching edge point algorithm delineates edge points not lying on the boundary for removal from the desired dark regions. Thereafter, the region between any two matching edge points is filled in with non-zero pixels to establish edge-based segmentation. In a preferred embodiment of the invention, only edge points whose directions are primarily oriented co-linearly with the scanline are sought to permit the detection of matching front wall and back wall pairs of a bladder cavity, for example the left or right ventricle.

Referring again to FIG. 11, results from the respective segmentation procedures are then combined at process block 314 and subsequently undergoes a cleanup algorithm process at process block 316. The combining process of block 214 uses a pixel-wise Boolean AND operator step to produce a segmented image by computing the pixel intersection of two images. The Boolean AND operation represents the pixels of each scan plane of the 3D data sets as binary numbers and the corresponding assignment of an assigned intersection value as a binary number 1 or 0 by the combination of any two pixels. For example, consider any two pixels, say $pixel_A$ and $pixel_B$, which can have a 1 or 0 as assigned values. If $pixel_A$'s value is 1, and $pixel_B$'s value is 1, the assigned intersection value of $pixel_A$ and $pixel_B$ is 1. If the binary value of $pixel_A$ and $pixel_B$ are both 0, or if either $pixel_A$ or $pixel_B$ is 0, then the assigned intersection value of $pixel_A$ and $pixel_B$ is 0. The Boolean AND operation takes the binary any two digital images as input, and outputs a third image with the pixel values made equivalent to the intersection of the two input images.

After combining the segmentation results, the combined pixel information in the 3D data sets In a fifth process is cleaned at process block 316 to make the output image smooth and to remove extraneous structures not relevant to bladder cavities. Cleanup 316 includes filling gaps with pixels and removing pixel groups unlikely to be related to the ROI undergoing study, for example pixel groups unrelated to bladder cavity structures. Thereafter, sub-algorithm 302 continues to process block 322 to confirm that the spherical-like cavity is a bladder. Preprocessing sub-algorithm 302 is then completed and exits to sub-algorithm 340.

Figure 12:
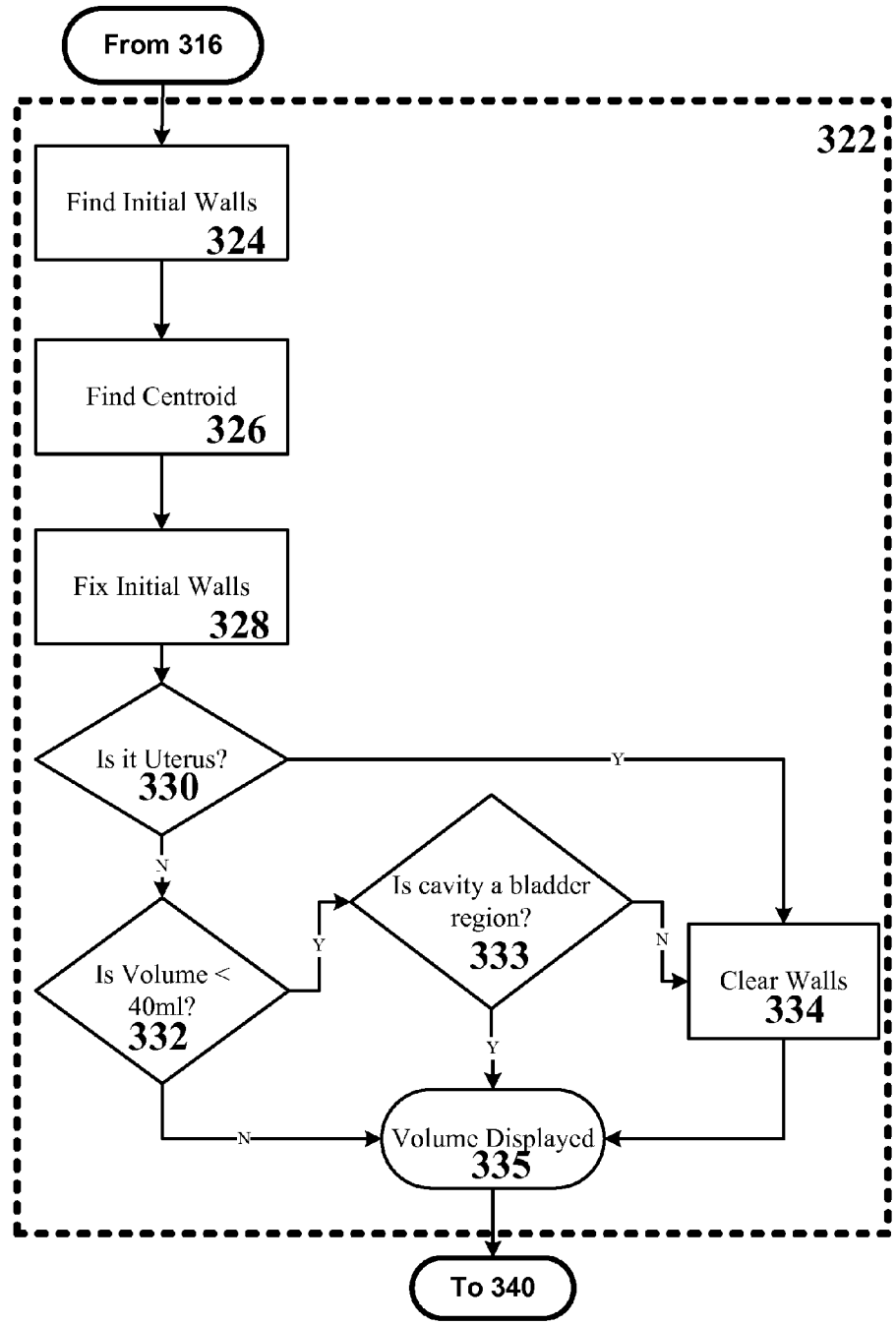
FIG. 12 is an expansion of sub-algorithm 322 of FIG. 11.

FIG. 12 is an expansion of sub-algorithm 322 of FIG. 11. The sub-algorithm 322 is comprised of five process and three decision routines to assess whether the spherical-like cavity defines a uterus. The first process block is block 324 and is called Find Initial Wall. From block 324 is block 326, Find Centroid. Thereafter, block 328 is Fixed Initial Walls. After Fix Initial Walls 328 is a decision diamond 330 with the query, "Is it uterus?" ? If the answer is affirmative for a uterus, that is "yes", the next process is Clear Walls block 334. Thereafter, the volume is displayed on the transceiver 10A,B in process block 335 and the sub-algorithm 322 is completed and continues to sub-algorithm 340. If the answer is negative for a uterus, that is "No", the sub-algorithm 322 continues decision diamond 332 in which the question is asked, "Is volume less than 40 ml.?" If the answer is "no" to the decision diamond 332 then the volume is displayed on the transceiver 10A,B at process block 335 and sub-algorithm 322 is completed and continues to sub-algorithm 340. If at decision diamond 332 the answer is "yes" to the query, "Is volume less than 40 ml.?", then sub-algorithm 322 continues to decision diamond 333 having a query "Is cavity a bladder region?" If the answer is "no" then the sub-decision diamond 333 proceeds to the Clear Walls of block 334 and thence to Volume Displayed at process block 335. If, at the decision diamond 333, the answer is "yes" to the query, "Is cavity a bladder region?" then the volume is displayed at process block 335 and sub-algorithm 322 continues on to sub-algorithm 340. In sub-algorithm 322, an interface line is overweighed on the B-mode scanplane image substantially similar to scanplane 42 to approximate an initial location for an cavity-tissue interface wall, as for example, a cavity-tissue interface of a uterus or a bladder. This initial interface line is used as a seed or initial reference point in which to further use as a basis to adjust the determination for the front and back walls of the spherical-like cavity. That is the processes within 322 are used to refine the initial wall point locations to a more highly resolving front and back wall layer positions, removing the outliers and to fill in any gaps in the cavity-tissue interface locations. Furthermore, in this algorithm, the detected region in the scan plane is determined to be or not to be a bladder or a uterus. This occurs specifically when the transceiver 10A,B indicates that the scan is for a female. If the cavity region is found to be a uterus, it is cleared and a zero volume is displayed. For a non-uterus cavity region, such as a bladder, if the volume is very small, then checks are made on the size of a signal characteristic inside the detected cavity region to ensure that it is a bladder and not another cavity-tissue interface. If, a region is indeed a bladder cavity region it is computed and displayed on the output display 16 of transceiver 10A,B and/or computer display 54.

Figure 13:
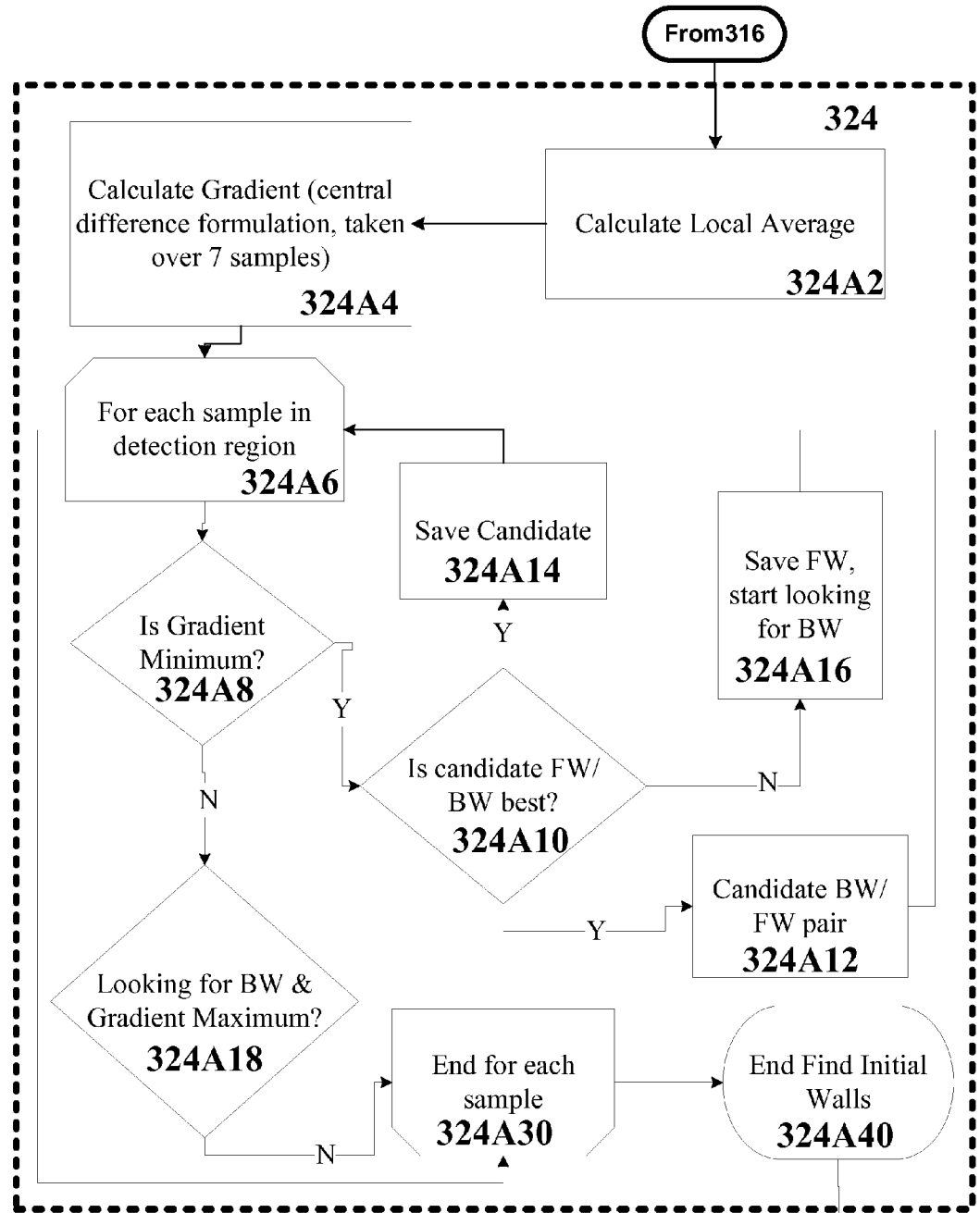
FIG. 13 is an expansion of sub-algorithm 324 of FIG. 12.

FIG. 13 is an expansion of sub-algorithm 324 of FIG. 12. The sub-algorithm 324 is comprised of 11 processes loops, decisions, and terminators enters from process block 16. Sub-algorithm 324 begins with process 324A2 in which the Local Average is calculated for the 15 to 16 samples. Next is block 324A4 in which the gradient is calculated using a central difference formulation and has taken over seven sample sets. The process at block 324 then proceeds to a beginning loop limit 324A6. In block 324A6, each sample is examined in a detection region. Thereafter, at decision diamond 324A8, the query is, "Is gradient minimum?" If the answer is "no" then another query is presented at decision diamond 324A18, the query being, "Looking for BW and gradient maximum?" BW stands for back wall. If the answer to the query in block 324A18 is "no" then the end of the loop limit is proceeded to at block 324A30. Thereafter, from the end of the loop limit at 324A30, the terminator end find initial walls are reached at block 324A40. Returning now to the decision diamond 324A8, if the answer to the query, "Is gradient minimum?" "yes" then another query is presented in decision diamond 324A10. The query in 324A10 is "Is candidate FW/BW best?" FW is a front wall and BW is back wall. If the answer to the query in block 324A10 is "no", then the process 324A62 is used in which the front wall is saved and another back wall is looked for. If the query to in 324A10 is "yes" then the process is Save Candidate occurs at block 324A14. Thereafter, the process returns to beginning loop 324A6 to resume. Returning to the decision diamond 324A10, should the answer be "yes" to the query, "Is candidate FW/BW best, then sub-algorithm 324 continues to process 324A12 in which the candidate is assigned as a pair for the "back wall/front wall." Thereafter from block 324A12 is returned to the beginning loop 324A6 and then the process will then terminate at end of each sample at end loop 324A30 and thence to terminator 324A40 for end find initial walls sub-algorithm. Sub-algorithm 324 attempts to find the best front wall and back wall pair for the inner and outer wall layer plotting points. The best front wall and back wall pair in each scan line is defined as the front wall and back wall pair for which the difference in the back wall gradient and front wall gradient sometimes referred to as the tissue delta, is the maximum and the smallest local average between the front wall and back wall pair is the minimum for the pixel values. Sub-algorithm 324 then exits to process block 326.

Figure 14:
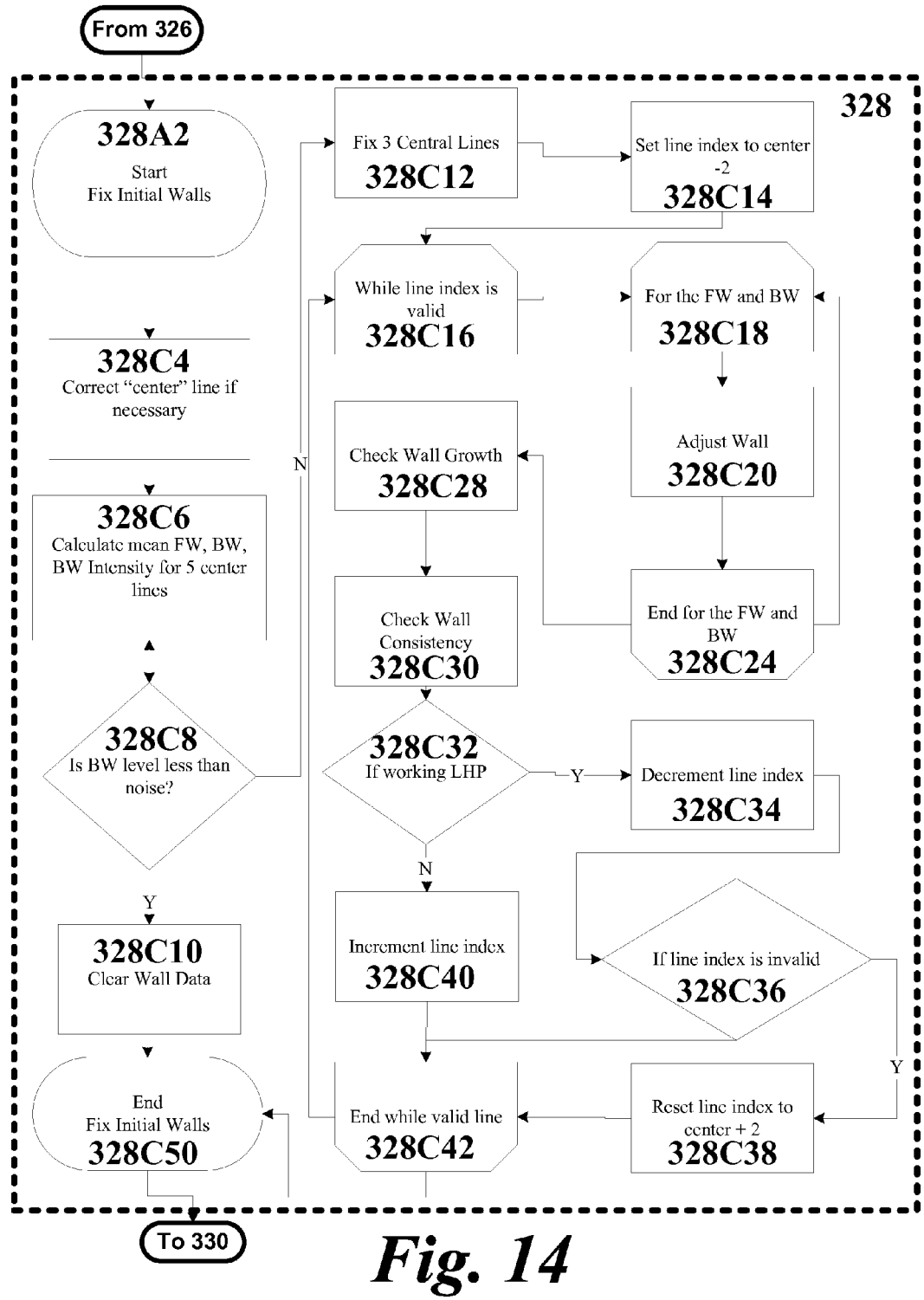
FIG. 14 is an expansion of sub-algorithm 328 of FIG. 12.

FIG. 14 is an expansion of sub-algorithm 328 of FIG. 12. Sub-algorithm 328 is comprised of several processes decision diamonds and loops and is entered from process block 326. Sub-algorithm 324C is comprised of several processes decision diamonds and loops. Sub-algorithm 324C operates on a scanplane by scanplane basis where the first scanplane to be processed is one that is closest to the central aid of the initial walls and then the remaining scanplanes are processed moving in either direction of that initial scanplane. Sub-algorithm 324C begins at block 324C2 referred to as Start Fix Initial Walls. The first process is at block 324C4 in which the center line is corrected if necessary. The center line is defined as the line on that scanplane with the maximum gradient difference between the front wall and the back wall. The correction of the front wall and the back wall location at any line is carried out by a match filtering like step where the best location within a search limit is defined as the one for which the difference between points immediately outside the bladder and points immediately inside the bladder is maximum. Of course, this applies to any organ other than the bladder, as the bladder is used here as an example of a particular embodiment. Thereafter, at block 324C6, the front wall and back wall means are calculated for five central lines. The pixel main intensity is computed and if this intensity is less than expected from the noise at that depth, the lines are cleared and the algorithm proceeds to the next plane as shown in decision diamond 324C8 to the query, "Is BW level less than noise?" where BW means the back wall (or posterior wall) of the bladder. If the answer is "yes" to this query, at block 324C10, the process Clear Wall Data is initiated and from that proceeds to terminator 324C50 End Fix Initial Walls. Returning to the decision diamond 324C8, if the answer is "no" to the query, "Is BW level less than noise?" then the sub-algorithm 324C proceeds to the process at block 324C12 described as Fix 3 Central Lines. From this point through the end of sub-algorithm 324C, the purpose is first correct the lines to the left of the central lines, called the left half plane (LHP) until either the edge of the bladder or the edge of the ultrasound cone is found. After the algorithm corrects the LHP, it proceeds to correct the lines to the right of the central lines, called the right half plane. Because the same steps are used for all lines, regardless of their position to the left of center or to the right of center, the process blocks 324C16 through 324C42 are used for both the LHP and once for the right half plane. The "line index" of process 324C14 indicates an identifier for the current line that is processed. The line index is set to 2 indices less than the center line to start processing the LHP. The looping procedure started in block 324C16 continues looping while the line index is a valid index (i.e. it corresponds to a scanline). Sub-loop 324C18 is started with the intent of adjusting the initial wall locations, sub-process 324C20, to their correct location if any correction is necessary. This loop, terminated at process 324C24, completes two iterations. The first iteration uses sub-process 324C20 to correct the front wall of the bladder on the current line and the second iteration to correct the back wall of the bladder, although the ordering of which wall is corrected first can be interchanged. Once the wall locations have been corrected of the current line have been corrected, sub-algorithm 324C proceeds to sub-process 324C28, "Check Wall Growth". This sub-process ensures that the length of the scanline that intersects the bladder in the current line does not grow significantly with respect to the previous line that has already been corrected. In the preferred embodiment, the length of the scanline intersecting the bladder is constrained to be less than 1.125 times longer than in the previous line. If the loop bounded by sub-processes 324C16 and 324C42 is being applied to the LHP, then the previous line is one index number greater than the current line index. Otherwise the previous line index is one index number less than the current index. After completing sub-process 324C28, sub-process 324C30 "Check Wall Consistency" verifies that the portion of the current scanline that intersects the bladder overlaps the portion of the previous scanline that intersects the bladder. After completing sub-process 324C30, decision 324C32 queries "If working LHP?" (i.e. the loop bounded by terminators 324C16 and 324C42 is being applied to the lines left of center). If the answer to the query is yes, then the sub-process 324C34 "Decrement line index" decreases the line index by one index number. Decision 324C36 queries "If line index is invalid". The loop bounded by terminators 324C16 and 324C42 is applied to the next, and now current, scanline. If the decremented line index corresponds to an invalid value, the edge of the LHP has been reached. Sub-process 324C38 is called to reset the line index to the first line to the right of center that has not been adjusted. The loop bounded by terminators 324C16 and 324C42 can now be applied to the right half plane (RHP). Returning to decision 324C32, if the answer to the query is "No", sub-process 324C40 "Increment line index" results with the line index being increased by one index number. Loop terminator 324C42 cause the loop to return to 324C16 as long as the line index corresponds to an actual scanline. As soon as that condition is violated, the loop terminator can cause sub-algorithm 324C to proceed to the terminator 324C50, "End Fix Initial Walls" is completed and exits to process block 330.

Figure 15:
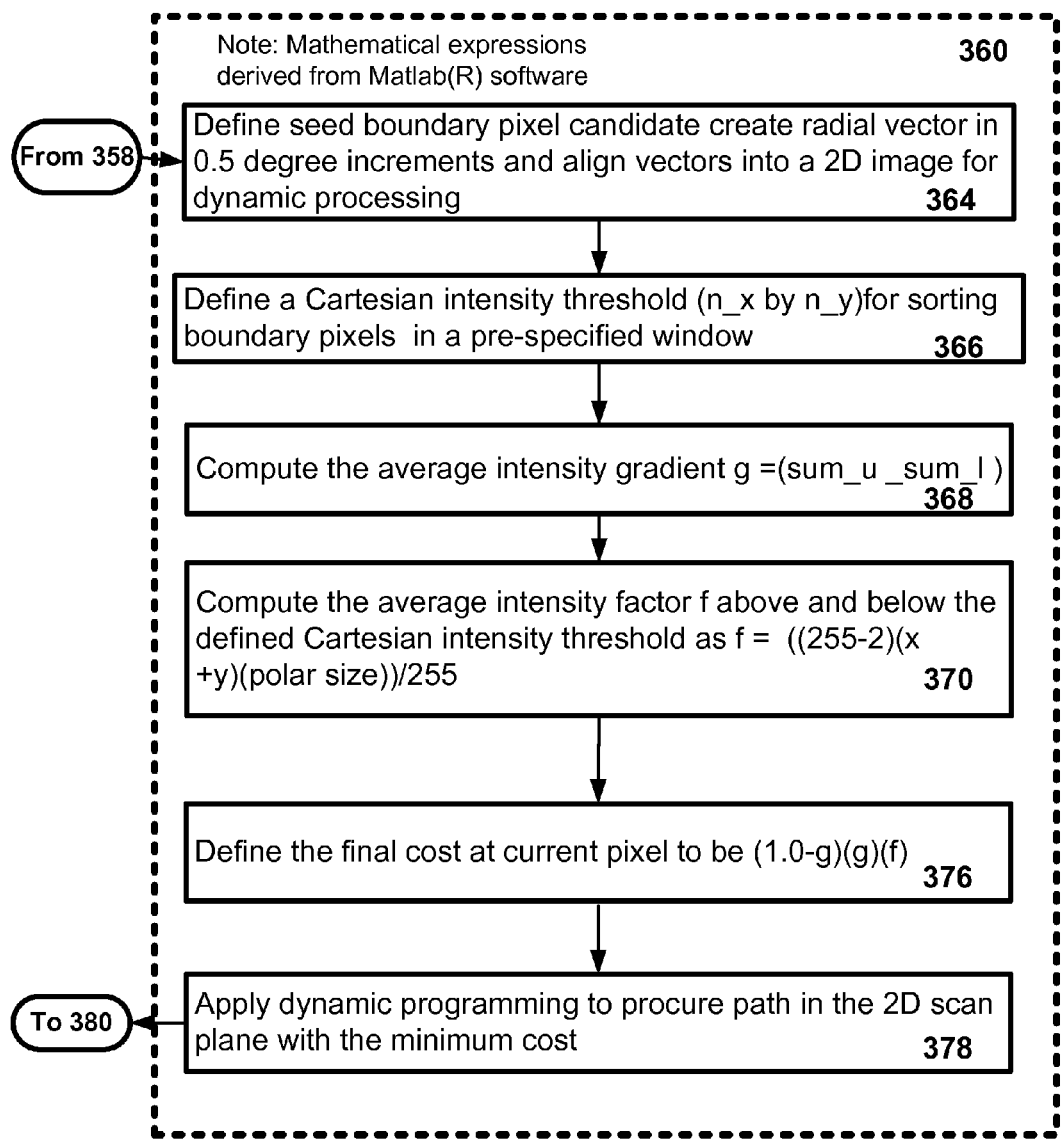
FIG. 15 is an expansion of sub-algorithm 360 of FIG. 10.

FIG. 15 is an expansion of sub-algorithm 360 of FIG. 10. In the following, we will show the intermediate result at each step of the method using a real bladder image. FIG. 15 is an expansion of sub-algorithm 360 of FIG. 10 and enters from process block 358. Beginning with process block 364, a seed boundary pixel candidate is defined and a radial vector in approximately 0.5 degree increments may be created from which vectors are aligned into a 2D image for dynamic processing. Smaller degree increments may be used to increase resolution with greater calculation cost and larger degree increments may be sued to lower calculation costs. With reference to Matlab® software herein incorporated by reference, the following processing blocks use mathematical expressions derived from Matlab® to describe the cost definition in terms of gradient term, g in which cost is equivalent as the sqrt($g_x*g_x+g_y*g_y$). Using these mathematical expressions, at process block 366, a Cartesian intensity threshold is defined as n_x by n_y for sorting boundary pixels in a pre-specified window or ROI pixel grid. Thereafter, at processing block 368, the average intensity of the boundary pixels is computed at sum_u for above the threshold and sum_1 for below the Cartesian defined threshold. Sub-algorithm 360 proceeds to process block 370 in which the average pixel intensity above and below the Cartesian defined intensity threshold is calculated. Thereafter, at process block 376, the final cost of a currently analyzed pixel is defined to be (1.0−g)(g)(f), in which g=sum_u−sum_1 and f=255*img[x+y*POLAR_SIZE])/255. This allows relatively high intensity pixels to have smaller f-factors and thus make is less possible to have a pixel on the least cost path. Sub-algorithm 370 is then completed with process block 378 to apply dynamic programming to pixels within pixel grid regions-of-interest to acquire the least cost pathway and thus extract the close contours defining the cavity-tissue/structure interface. Sub-algorithm 360 then exits to process block 380.

Figure 16:
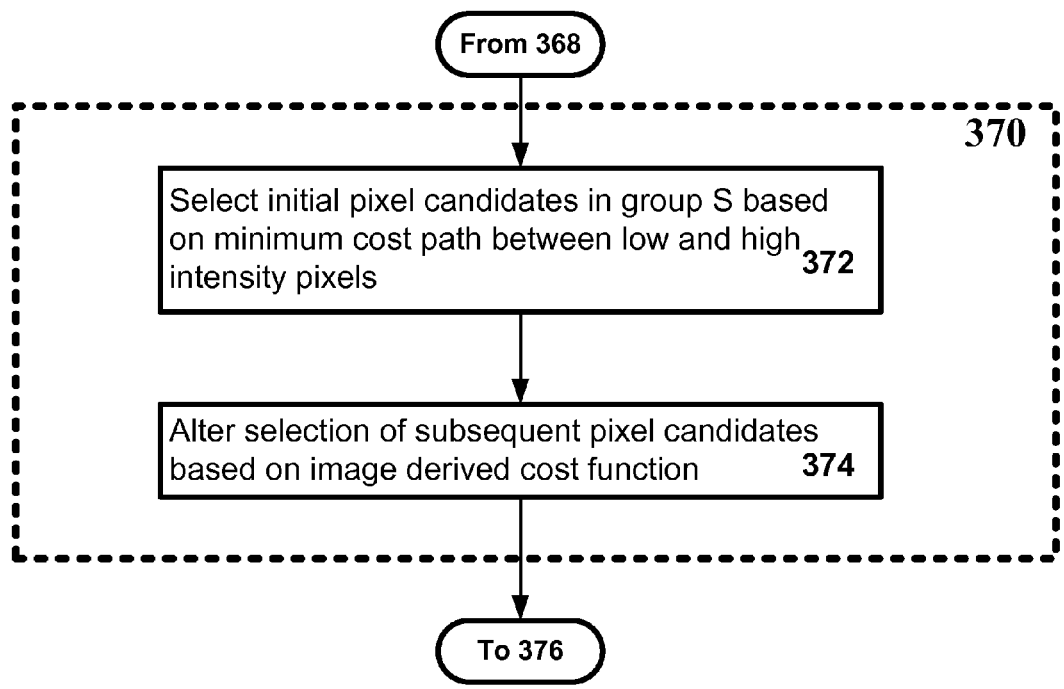
FIG. 16 is an expansion of sub-algorithm 370 of FIG. 16.

FIG. 16 is an expansion of sub-algorithm 370 of FIG. 16 to generate initial front and back wall pixel candidate points and enters from process block 348 and begins with process block 372. At process block 372, initial pixel candidates in group S are selected on minimum cost path between the low and high intensity pixels. Thereafter, at process block 374, selections of subsequent pixel candidates are made based on the image derived cost function. Sub-algorithm 370 is then completed with process block 374 to apply dynamic programming to pixels within pixel grid regions-of-interest to acquire the least cost pathway and thus extract the close contours of defining the cavity-tissue/structure interface. Sub-algorithm 370 then exits to process block 376.

Figure 17:
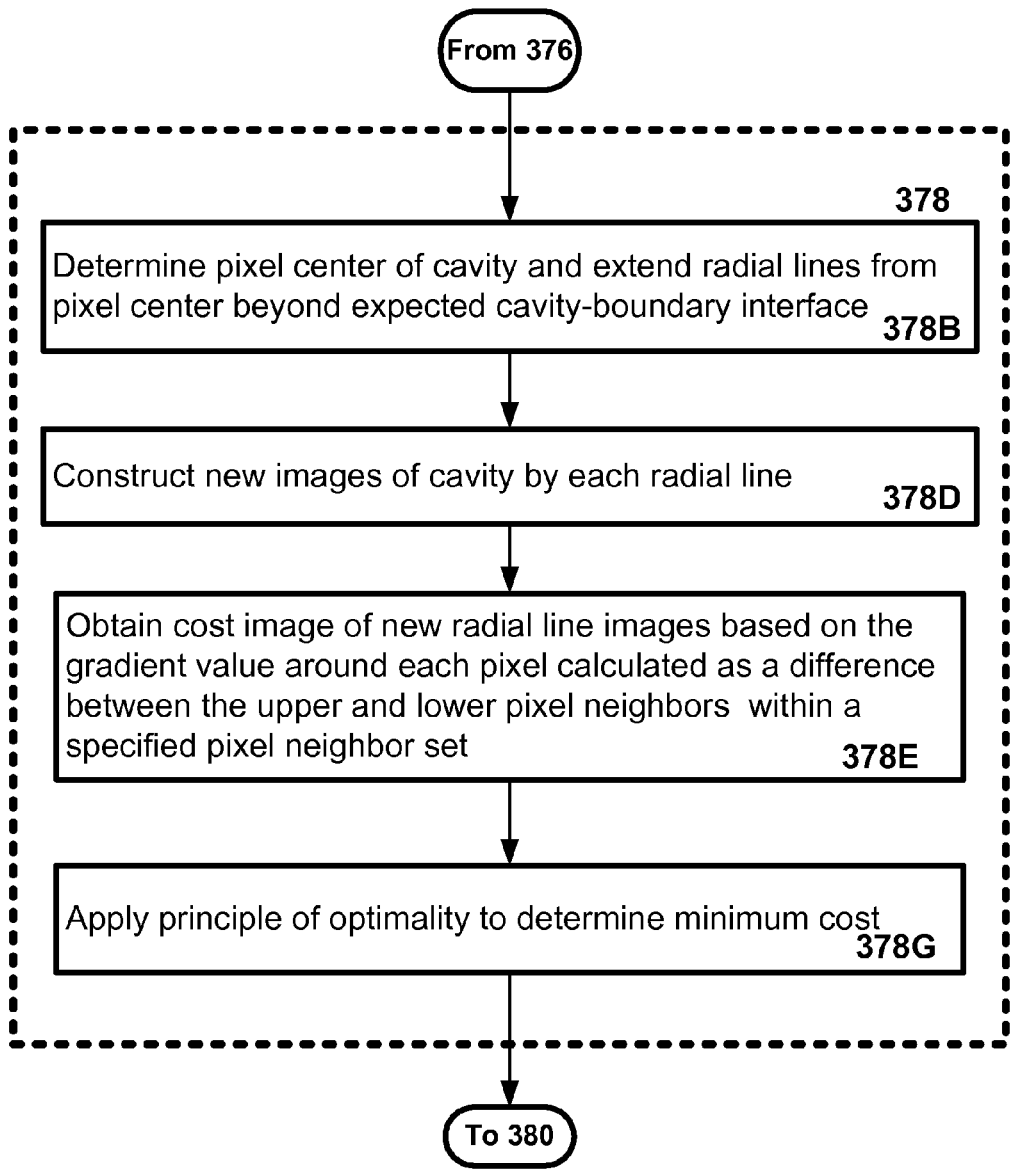
FIG. 17 is an expansion of sub-algorithm 378 of FIG. 15.

FIG. 17 is an expansion of sub-algorithm 378 of FIG. 15. Entering from sub-algorithm 376, sub-algorithm 378 begins with process block 378B, wherein the pixel center or center mass of a substantially spherical shaped cavity is determined, and radial lines are extended from the pixel center beyond the expected cavity-boundary interface. FIG. 21 below illustrates an example of process block 378B. Thereafter, at process block 378D, new images are procured along the radial lines and presented in pre-defined windows. FIG. 22A below illustrates an example of a window image. Then, at process block 378E, a cost image is obtained of each radial line image based upon the gradient value around each pixel. The gradient value is calculated as the difference between the upper and lower pixel neighbors with a specified pixel neighbor set. FIG. 22B below illustrates an example of a cost image. Thereafter, at process block 378G, the principle of optimality is applied to determine the minimum cost of the image window. FIGS. 22C and D below illustrates examples of the results of applying the principle of optimality in obtaining cavity-interface boundary tracings. Sub-algorithm 348 is then completed and exits to sub-algorithm 380.

Figure 18:
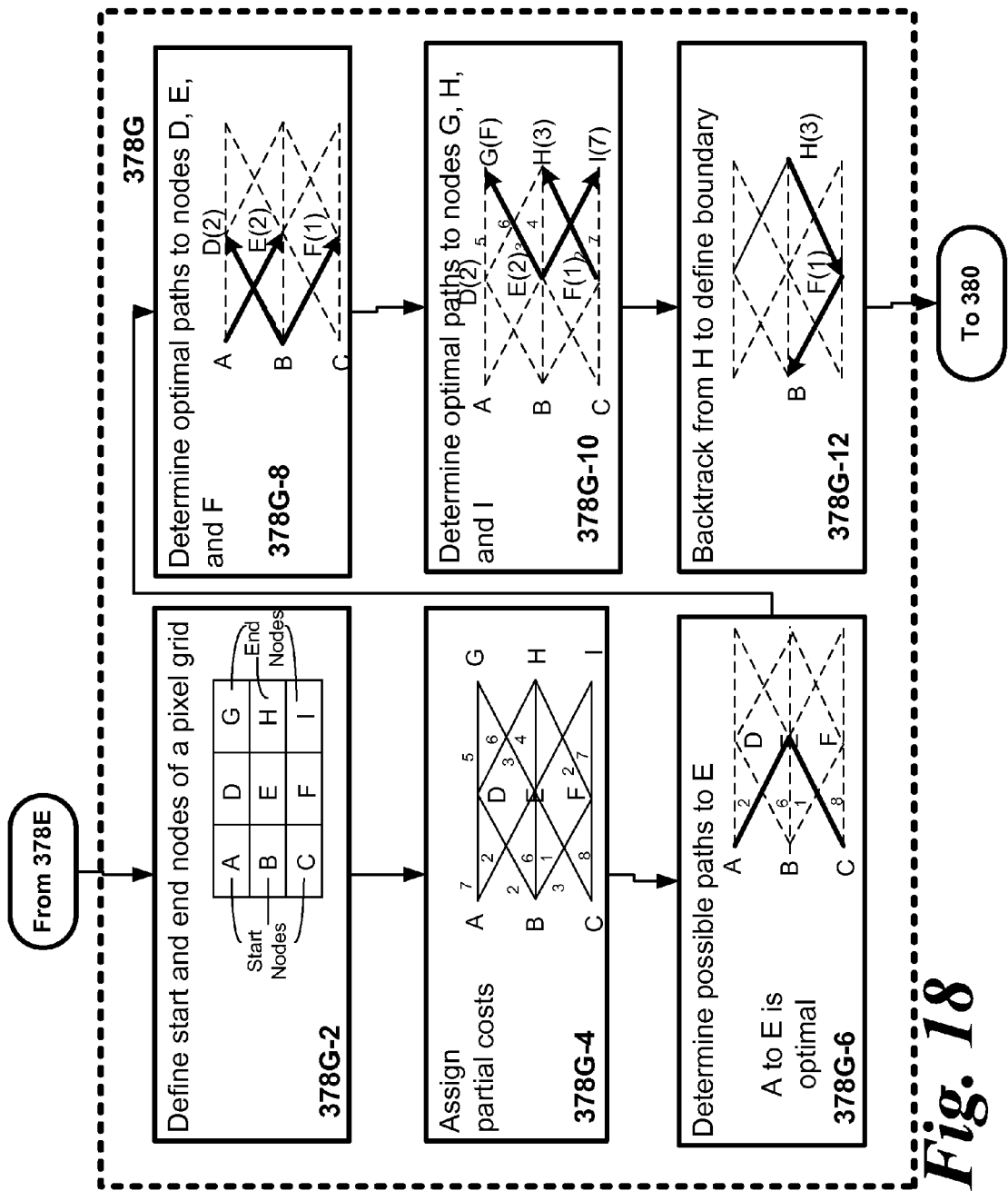
FIG. 18 is an expansion of sub-algorithm 378G of FIG. 17.

FIG. 18 is an expansion of sub-algorithm 378G of FIG. 17. Entering from sub-algorithm 378E, sub-algorithm 378G begins with process block 378G-2, wherein start and end nodes are defined as illustrated for a pixel grid having nodes A-I. Here start nodes A-C and end nodes G-I are defined. Thereafter, at process block 378G-4, partial cost values are assigned and distributed on the pixel grid as shown. How the cost values are defined, the situations in which employed, and how processed is described in FIG. 25 below. The next processing block is 378G-6, in which the possible paths to node E is mapped. Here path A-to-E is optimal as shown by the heavier lines. Thereafter, at process block 378G-8, the optimal paths to nodes D, E and F are determined, followed by process block 378G-10, in which the optimal paths to nodes G, H, and I are determined. Then, at process block 378G-12, the boundary of the interface between cavity and surrounding tissue or structures is defined by backtracking from node H. Sub-algorithm 378G is then completed and exits to sub-algorithm 380.

Figure 19:
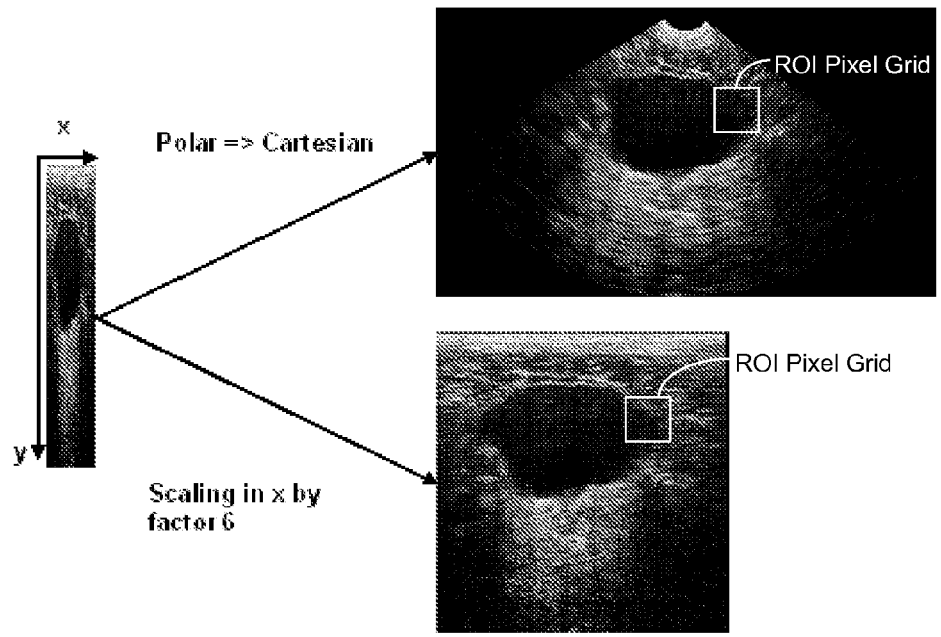
FIG. 19 illustrates an overlap of a pixel grid ROI upon a Cartesian transformed scan plane and a X-axis stretched scan plane.

FIG. 19 illustrates an overlap of a pixel grid ROI upon a Cartesian transformed scan plane and a X-axis stretched scan plane. The pixel grid ROI overlaps a portion of a bladder cavity dark region and brighter, surrounding echogenic tissue.

Figure 20:
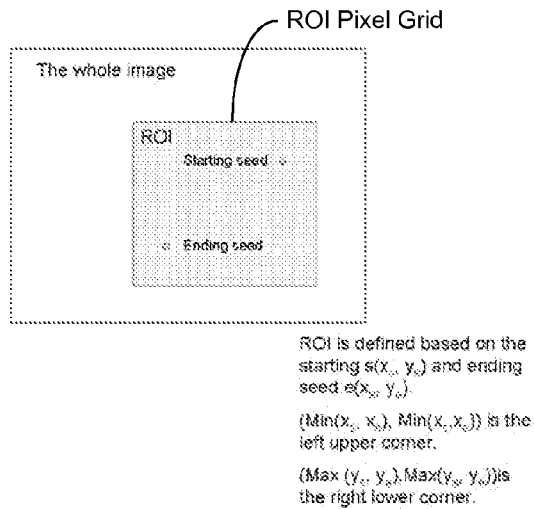
FIG. 20 schematically illustrates the pixel grid ROI of FIG. 19 in relation to the total 2D image.

FIG. 20 schematically illustrates the pixel grid ROI of FIG. 19 in relation to the total 2D image. The pixel grid ROI is defined based on the starting and ending seed candidates and includes pixel groupings having maximum and minimum intensity values described in Cartesian terms.

FIG. 21 is an image of a bladder cavity to determine the pixel center of the bladder cavity. Consistent with sub-algorithm 378, the mass center of the pixel population is approximately designated by the hollow, white circle. The mass center is determined from find centroid of processing block 326 of FIG. 12 above more fully described in co-pending U.S. patent application Ser. No. 11/061,867 filed Feb. 17, 2005, referenced above in the priority claim and fully incorporated by reference. From the circle, radial lines are extended beyond the expected cavity-boundary interface. The radial lines serve as guides to obtain sub-images for submission to dynamic processing illustrated in FIGS. 22A-D below and described in FIG. 25 below.

FIGS. 22A-D illustrates a sequence of images obtained from application of dynamic processing sub-algorithms 378 and 378G of FIGS. 17 and 18 above. Here a sampling of new images for the radial lines of FIG. 21 are constructed in FIG. 22A, then presented as a cost image in FIG. 22B, then a cavity boundary tracing, unsmoothed, in red in FIG. 22C is obtained using the principle of optimality described in FIG. 25 below, and a smooth version of the boundary tracing, in blue, is presented in FIG. 22D.

FIG. 22A is a cost image of FIG. 21. It is based on the gradient value around each pixel. The gradient is calculated as the difference between lower neighbor and upper neighbor. The size of the image window is pre-specified.

FIG. 22B is the dynamic programming or processing in which the optimal path in 2D of the cost image is obtained as a boundary-interface tracing having minimum cost and is shown in red.

FIG. 22C is the smoothed version of FIG. 22B in which the smoothing is derived by a neighboring window image. In this case the window is 30.

Figure 23:
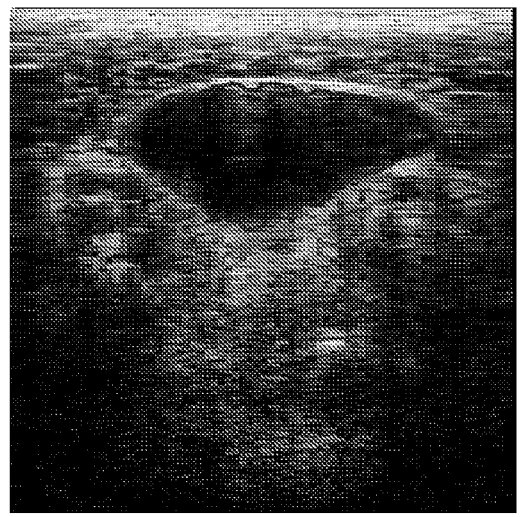
FIG. 23 illustrates a tracing overlap of the cavity boundary of FIG. 21 using dynamic programming.

FIG. 23 illustrates a tracing overlap of the cavity boundary of FIG. 21 using dynamic programming. A cavity boundary tracing is shown in blue and depicts the interface obtained from application of the principle of optimality described in FIG. 25 below.

Figure 24:
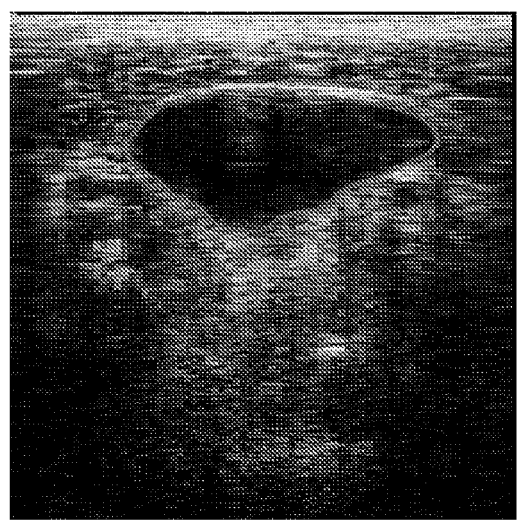
FIG. 24 illustrates a smoothed tracing overlap of the cavity boundary of FIG. 23.

FIG. 24 is a smoothed tracing overlap of the cavity boundary of FIG. 23. The smooth tracing is shown in red.

Figure 25:
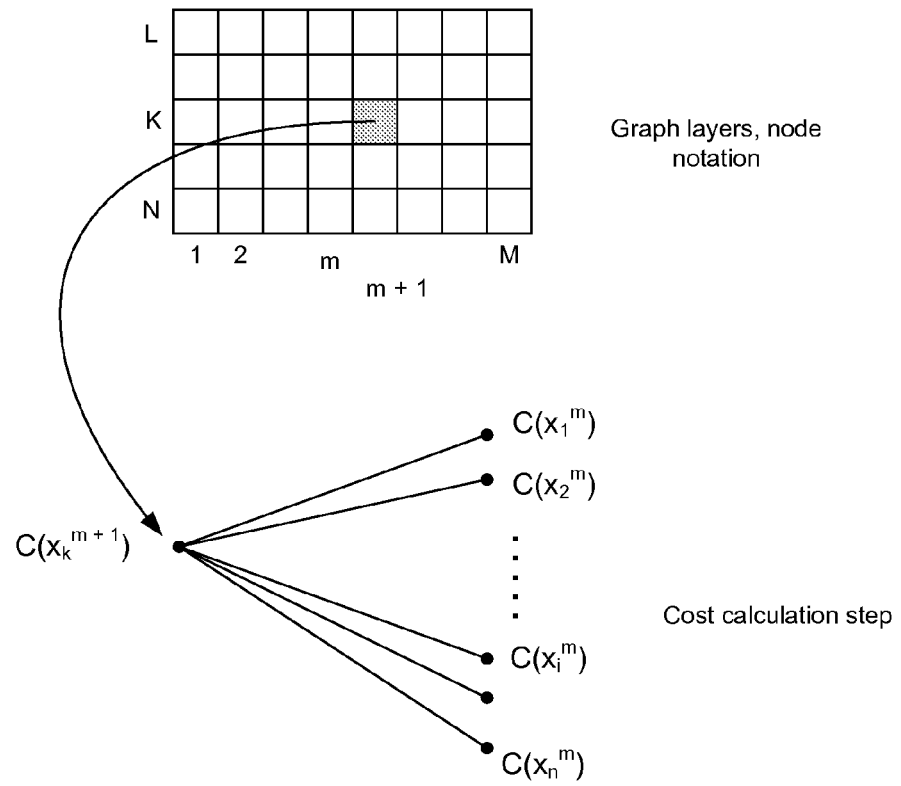
FIG. 25 illustrates the notation and cost calculation steps for the principle of optimality.

FIG. 25 illustrates the notation and cost calculation steps for the principle of optimality undertaken in securing the pixel boundary interface tracings overlap upon the scanplane cavity images presented in FIGS. 23 and 24. The principle of optimality asserts that there is an optimal path for boundary tracing by dynamic programming between endpoints whatever the path to the node E assumes. It searches for optima of functions in which not all variables are simultaneously interrelated. That is, if the optimal start-point and end-point transit through E, then both end-points are optimal. Should the graph have more layers, the process in applying the principle of optimality is repeated as necessary until one of the starting or stopping end-points is reached. The method for applying the principle of optimality begins with defining initial Cost in the form $C(x_i^1)$ for all nodes in the first graph layer, I=1, ... n and partial path costs $g^m$ (I,k), m=1 . . . , M−1, then perform a series of cost calculation steps using the equation $C(x_k^{m+1}) = \min_{i=-1, 0, 1}(C(x_{k+i}^m) + g^m(i, k)$ in which m to M series are repeated and the k to n in the graph layer m series are repeated, the pointer is set to the $x_k^{m+1}$ node and the $x_i^{m*}$, where * denotes the optimal predecessor. Thereafter, the optimal node $x_i^{M*}$ in the last graph layer M is obtained and an optimal pathe is procured by backtracking through the pointers from $x_k^{M*}$ to $x_i^{1*}$. For further information, see Sonka et. al (M. Sonka, V. Hlavac, R. Boyle, Image Processing, *Analysis, and Machine Vision*, 1998, ISBN 0-534-95393-X), herein incorporated by reference.

Figure 26:
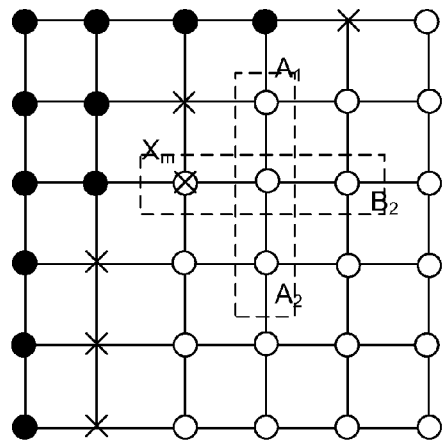
FIG. 26 graphically and pictorially illustrate the fast matching method used in block 700.

FIG. 26 graphically and pictorially illustrate the fast matching method used in block 700. Employing the fast marching, level set method of Sethian, (J. A. Sethian. A fast marching level set method for monotonically advancing fronts. Proc. Nat. Acad. Sci., 94(4), 1996) herein incorporated by reference, seed cavity-tissue/structure seed points are automatically generated by gradient calculations of pixel group intensities using arrival time minimums determined by Eikonal equations applied to the pixel gradients at the 2D scanplane level, and for scancones in 3D space, a Euclidian transform function is applied. Here a hypothetical grid having 36 trial pixel points are subjected to analysis using the fast marching method and are classified into far, trial, accepted, and minimal arrival time $X_m$. Once the point $X_m$, is determined, it is moved into the accepted category and the arrival times of neighboring pixels is updated. The updating of neighbors is if a given pixel is classified as far, it is moved to the Trial set. When the $u(x)=\min\{(u)x, u_{xj}x_m(x)\}$ with $u_{xj}x_m$, (x) is computed as follows: Let (A1,A2) and (xm, $B_2$) be two pairs of the opposite neighbors of x. then if uxm<$uB_2$, then uxj=min(ua1, uA2); if uxj<uxm, then $u_{xj}x_m(x)$=½(uzj+uxm+sqrt($2t^2$−(uxj−uxm$)^2$); else uxjsm(x)+uxm+Tx; end if else uxjxm(x)=infinity.

Figure 27:
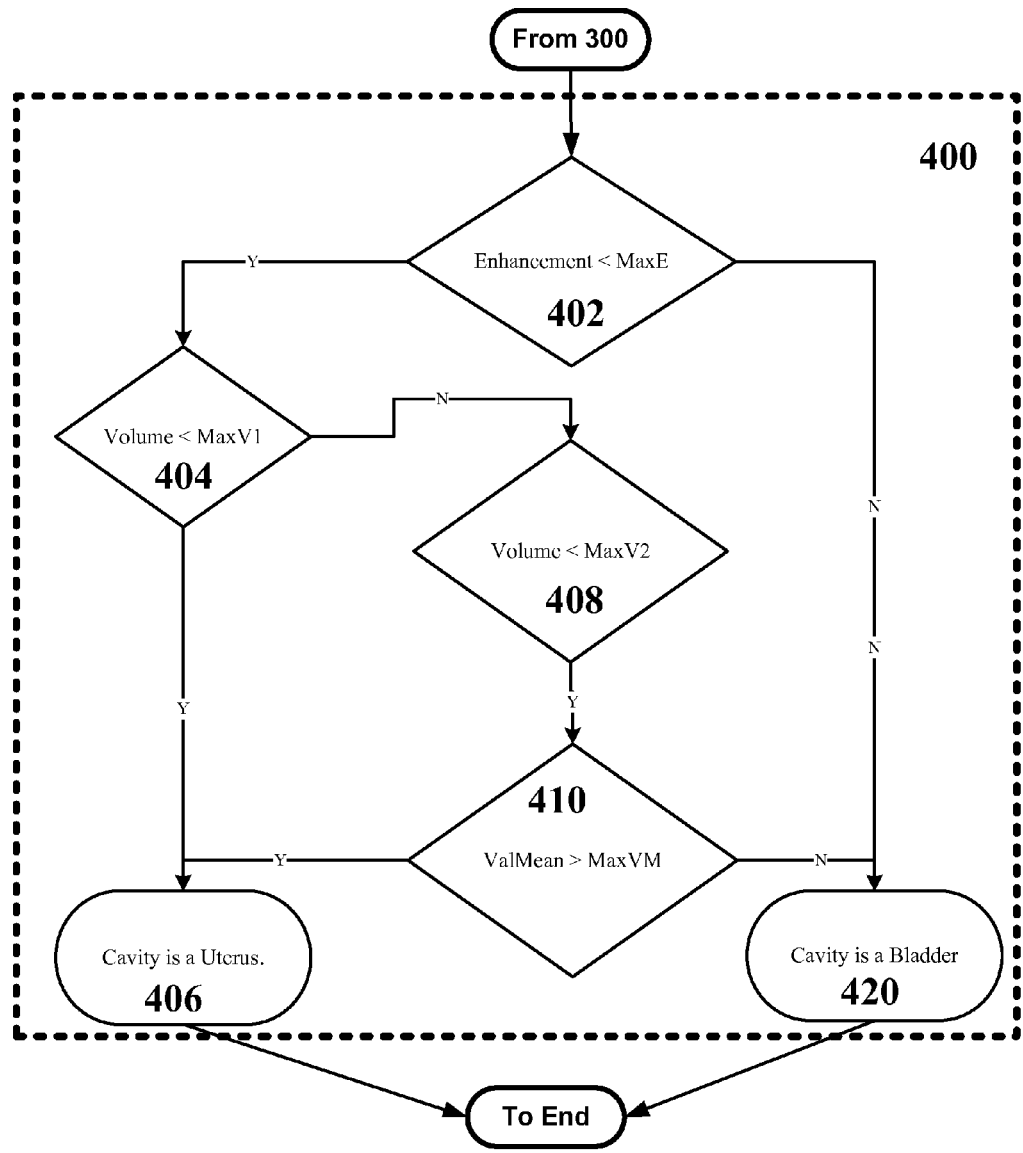
FIG. 27 is an expansion of the sub-algorithm 400 of FIG. 7.

FIG. 27 is an expansion of the sub-algorithm 400 of FIG. 7. The procedures within sub-algorithm 400 provide a decision tree used for ascertaining whether a uterus or bladder cavity has been detected. The definitions of the abbreviations in the flow chart blocks are Max E, Max V1, Max V2, ValMean, and MaxVM. Max means maximum, E means enhancement, V1 means volume 1, V2 means volume 2, ValMean refers to a measurement of the minimum local average pixel intensity of the region inside the region identified as urine inside the bladder, Max VM is a pre-defined threshold against which VALMEAN is tested. If VALMEAN is greater than MAXVM, the region identified as urine inside the bladder isn't really urine and the boundaries are actually an outline of the uterus. The sub-algorithm 400 begins from sub-algorithm 300 in which a decision diamond 402 is reached to determine if Enhancement<MaxE (maximum enhancement). If the answer is "yes" for enhancement, then another decision diamond 404 is reached and the query to determine whether the Volume<Max V1 (maximum Volume 1) is made. If the answer is "yes" to this query, then the determination at terminator 406 is reached and the organ cavity that is being examined is a uterus and sub-algorithm 400 is completed and exits to the end of master algorithm 120 of FIG. 7. If, at decision diamond 404 the answer is "no" to the query Volume<Max V1, then another decision diamond 408 is reached in which the query is, "Is the Volume<Max V2?" (Maximum Volume 2). If the answer is "yes", then the next decision diamond is 410 in which the query, "Is the ValMean>MaxVM. If the answer is "yes", then terminus 406 is reached and the organ cavity being viewed is the uterus. If the answer is "no", then terminus 420 is reached and the organ cavity being viewed is a bladder. Thereafter, sub-algorithm 400 is completed and exits to the end of master algorithm 120 of FIG. 7. Returning back to decision diamond 408, if the answer is "no", then to the query, "Is the volume<than MaxV2", then the answer is a bladder is being viewed as indicated by the terminus 420." Depending on the hardware platform used for the various embodiments of the transceiver 10A,B the decision tree for the sub-algorithm 400 of FIG. 7. The values used are described in the table below that has several headings of parameter name, description, pixel value for the transceiver 10A,B and a pixel values.

FIG. 28 is an expansion of sub-algorithm 600 of master algorithm 120 of FIG. 7 concerning acquisition echogenic signal data sets of non-spherical like, i.e., column-like or tubular like cavities, for example blood or lymph vessels having variable fluid flow rates. The acquisition of tubular echogenic signal data sets of sub-algorithm 600 also applies to the larger blood vessels having pipe-like characteristics, for example, the abdominal aorta and any bulges or aneurysms thereto. Sub-algorithm 600 flows from decision diamond 150 and begins with process block 602 by applying placing the transceiver 10A or 10B firmly against the abdominal dermal surface of a subject that is nearby the ROI, for example abdominal aorta that is not being blocked by the bony structures of the spinal column. By "nearby" is meant that at least a portion of the pipe or tube-like cavity is visible on either the transceiver's 10A' s or 10B's display 16, and/or computer display 54. Thereafter, at process block 606, radio-frequency ultrasound is transmitted to the ROI having spherical-like and/or column-like cavities. The ultrasound frequency may be adjusted to accommodate transmission distances and tissue barriers that attenuate or absorb probing ultrasound in transit to and/or ultrasound echoes reflected from the abdominal aorta or similar fluid containing vessel. Following at process block 610, ultrasound echoes returning from the ROI are acquired by the transceivers and converted to signals, and the signals are presented as echogenic datasets on the transceiver display 16 and/or computer display 54. Thereafter, at decision diamond 618, a query is presented "Is cavity of ROI sufficiently in view?", and if affirmative, ie., sufficiently in view, for example the cavity is centered or otherwise discernable to acquire a 3D dataset, sub-algorithm 500 continues and is completed at process block 626 for acquisition of a 3D echogenic data set scanplane substantially similar to scan cone 40 of FIG. 1A or scan cone 30 of FIG. 2. The 3D echogenic data set may be derived from the fundamental ultrasound frequency or harmonic thereof. If the answer is negative for sufficiency for cavity presentation, then sub-algorithm 200 resumes to process block 622 in which the transceiver 10A or 10B is moved to a new anatomical location, i.e., a new dermal surface location having an unobstructed view of the abdominal aorta, for reacquisition of tube-like cavity image. The image reacquisition loop from process blocks 602 through 622 is repeated until an affirmative tube or pipe-like cavity image is acquired for completion at process block 626. At least one scan cone image is obtained at process block 626. In the case of multiple scan cones 3D data sets, the 3D images may be registered and merged together to provide larger 2D and 3D views of the abdominal aorta and any aneurysm thereto. The 3D datasets may be formed from echoes derived from the probing fundamental ultrasound frequency, or any harmonic thereof. Sub-algorithm 500 is then completed and exits to sub-algorithm 700.

FIG. 29 is an expansion of sub-algorithm 700 concerning the fast marching live wire or level set active contour method processing of echogenic signals of master algorithm 120 illustrated in FIG. 7. From sub-algorithm 600, sub-algorithm 700 begins with pre-processing of echogenic signals of image data sets at process block 702 using anisotropic diffusion of Perona and Malik (P. Perona and J. Malik, Scale-space and edge detection using anisotropic diffusion, IEEE Transactions on Pattern Analysis and Machine Intelligence, 23(7), pp. 629-639, 1990) herein incorporated by reference. The anisotropic diffusion method may be engaged by use of programming provided by Visualization Toolkit® (VTK) available from Kitware, Inc., Clifton Park, N.Y., USA. After signal pre-processing, initially acquired polar coordinate 2D ultrasound images are converted to either a Cartesian format, or stretched in the X-axis direction in process block 740 so that roundness may be conferred to the teardrop shaped polar coordinate images more amenable for segmentation by the level set-live wire algorithm. Transformation to Cartesian coordinates may be achieved using Matlab® from MathWorks, Inc., Natick, Mass., USA, herein incorporated by reference, using the command file polarstretch.m. Thereafter, at process block 754, front and back wall candidate pixels are selected as starting and ending pixel grid seeds.

There are two different ways to use these wall candidates in level set frame works:

Fast marching live wire:
 All the wall candidates are ordered based on neighborhood relation. Use the frist one as the live starting point and the last on as the ending point for fast marching live wire method. The cost of the live wire is determined by the gradient information from all pixels on the wire. When the live wire is extracted and linked, the corresponding contour will be the corresponding boundary of the cavity.

Level set active contour:
 Use all the wall candidates, an initial contour is created. Then based on the level set active contour method, the initial contour will deform based on the force at each pixel on the contour. When specific criterion converges, the corresponding contour will be the final boundary of the cavity. The method can be used in 2D and can also be utilized in 3D space.

Once the pixel candidates are processed by the fast marching live wire or the level set active contours methods, sub-algorithm 700 continues to process block 760, where the mass centers are computed per process block 360. Thereafter, at process block 784, the pixels are connected having minimum travel time cost paths to determine the cavity-tissue interface of the cavity structure boundary or final contour determined by the level-set method. Then, sub-algorithm 700 concludes and exits to sub-algorithm 800.

Figure 30:
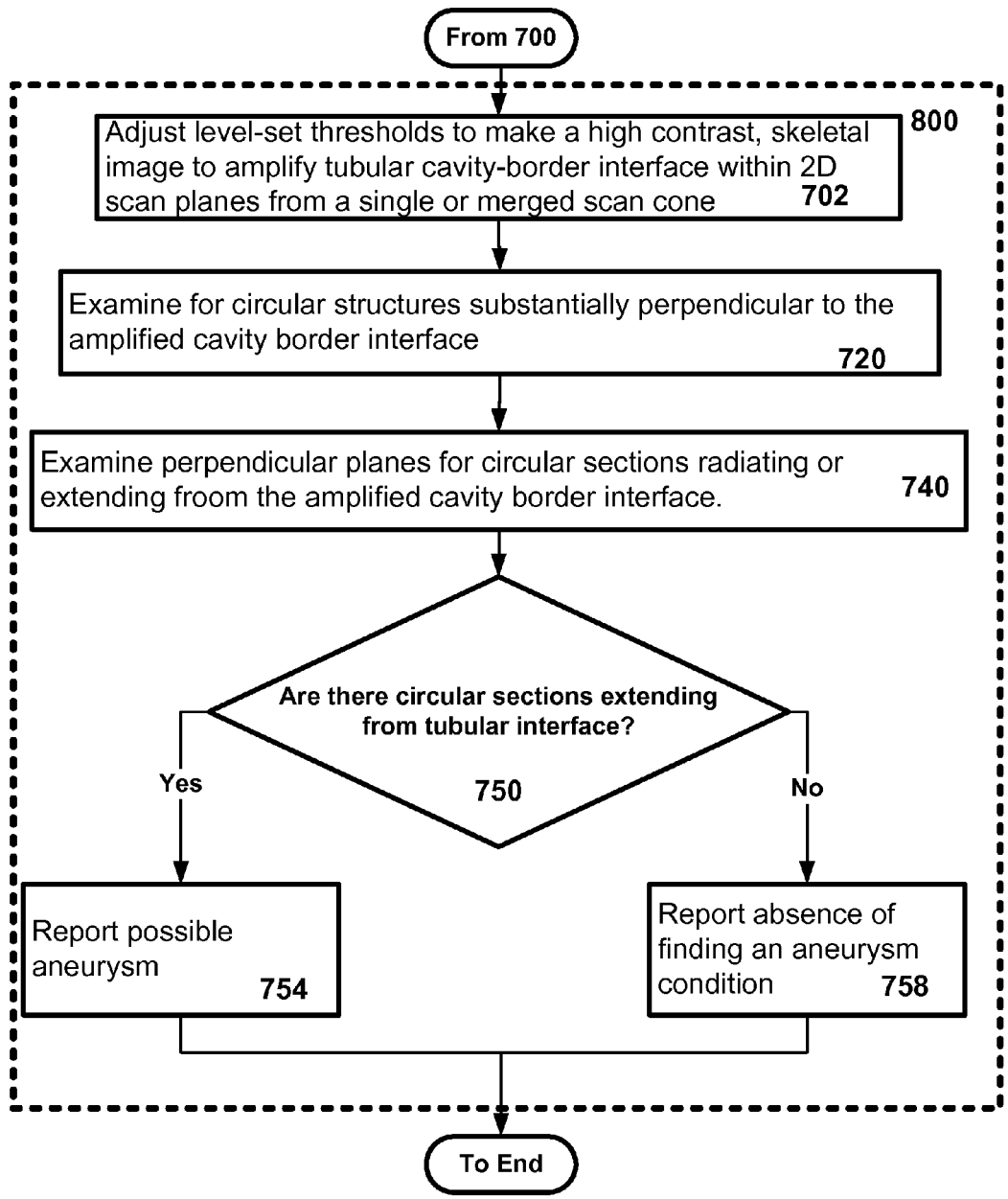
FIG. 30 is an expansion of sub-algorithm 800.

FIG. 30 is an expansion of sub-algorithm 800 the identification of a tubular imaged structure of master algorithm 120 illustrated in FIG. 7. From sub-algorithm 700, sub-algorithm 800 begins with processing block 802 in which level-set thresholds are adjusted to produce a high contrast, skeletal image to amplify the appearance of the tubular cavity-border interface within either a single scan plane or multiple scan plane from either a single scan cone or multiple scan cones in which the scan planes have been registered and merged together. Thereafter, at processing block 820, the scan plane having the high contrast tubular vessel interface is examined for any partial, circular-like structures that radiate, emerge, or otherwise bulge from the cavity-border interface at a substantially perpendicular angle to the tubular cavity-border interface. Upon examination, a decision diamond 850 is reached with the query "Are there circular sections extending from the tubular interface?". If affirmative, sub-algorithm 800 proceeds along the "Yes" pathway to process block 854 to report a possible aneurysm. If negative, sub-algorithm 800 continues via the "No" pathway to process block 858 to report an absence of finding an aneurysm condition. Thereafter, sub-algorithm 800 is completed and exits to the end of master algorithm 120.

Figure 31:
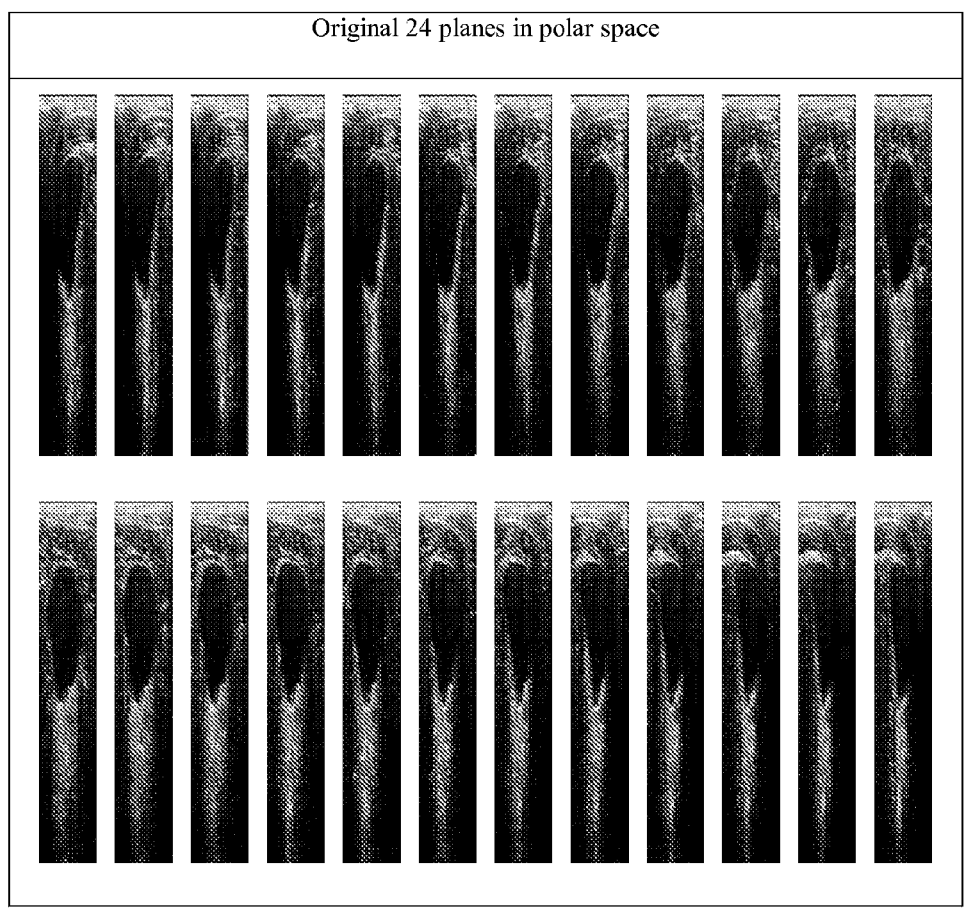
FIG. 31 is a 24-scanplane panel of bladder images presented in polar coordinates.

FIG. 31 illustrates a 24-scanplane panel of bladder images presented in polar coordinates. The teardrop shapes of the polar coordinate images are not round enough for to accurately extract close contours of circular cross-sections of substantially spherical cavities.

Figure 32:
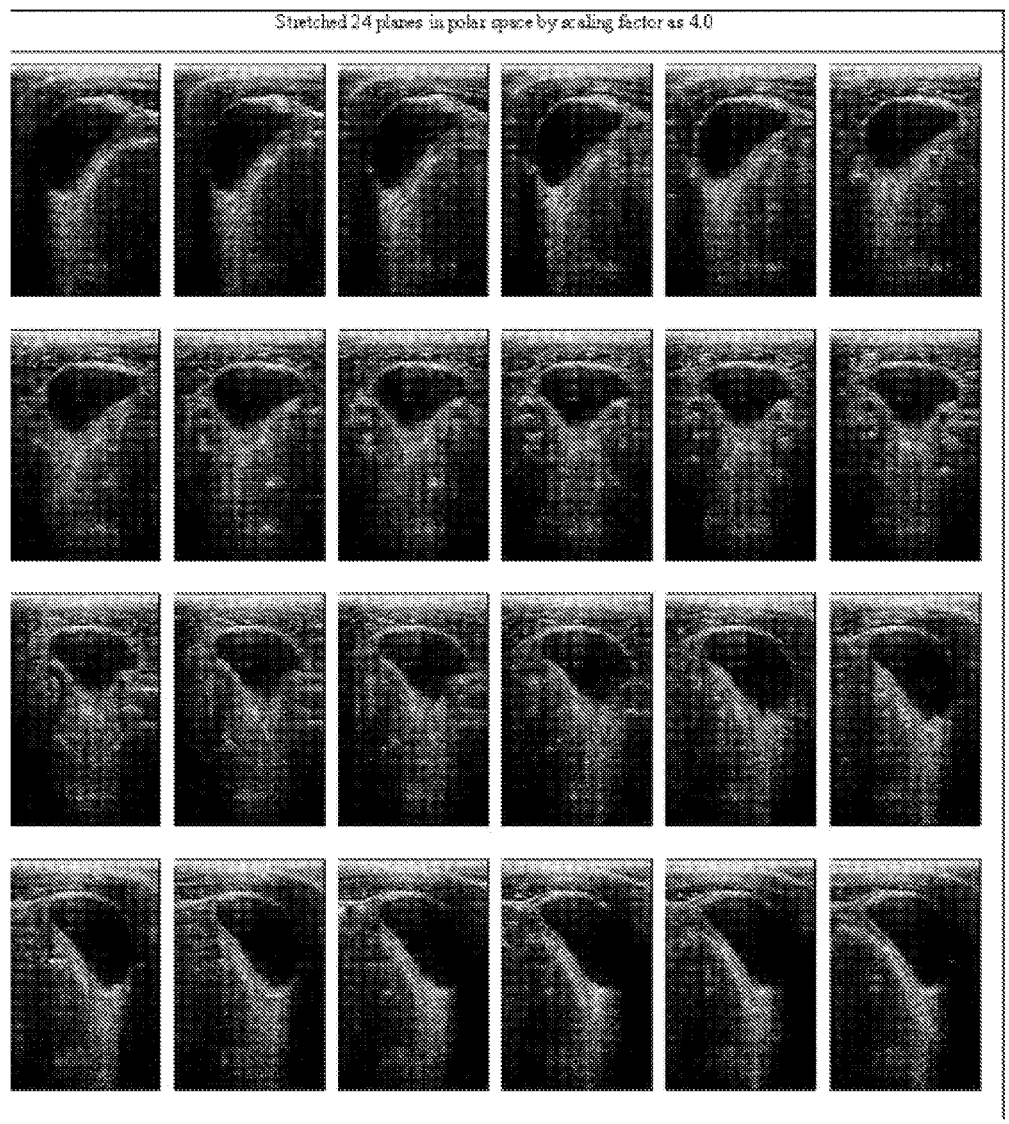
FIG. 32 is the 24-scanplane panel of bladder images of FIG. 26 stretched in the X-axis direction by a 4.0 scaling factor.

FIG. 32 is the 24-scanplane panel of bladder images of FIG. 31 stretched in the X-axis direction by a 4.0 scaling factor. The stretching provides enough roundness to the bladder images so that close contours in the curvature in the bladder 2D image cross-sections may be accurately extracted and be amenable for segmentation via the dynaminic programming algorithm of process block 700 of master algorithm 120 illustrated in FIG. 7.

Figure 33:
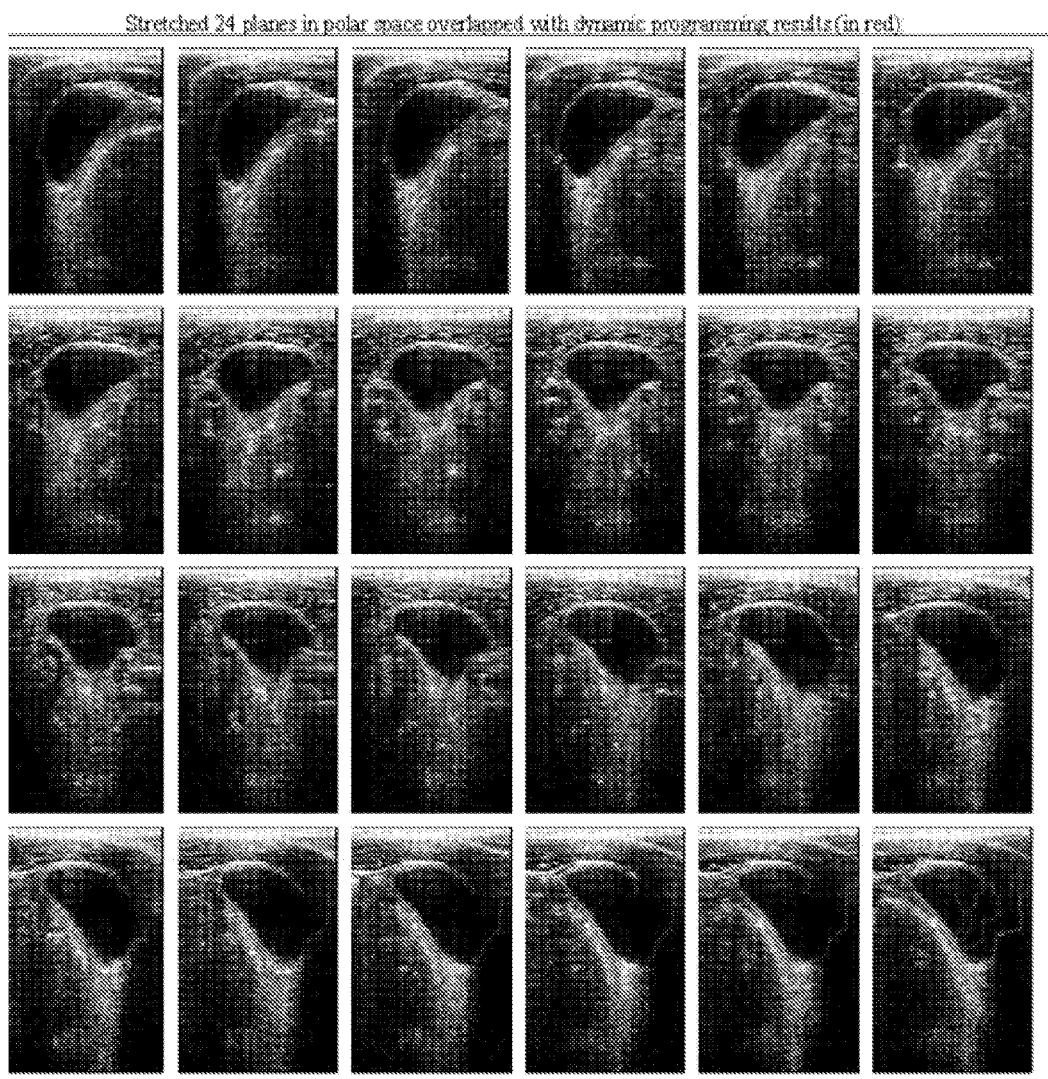
FIG. 33 is the segmentation of the bladder cavity-tissue interface of the X-axis stretched bladder images of FIG. 27.

FIG. 33 illustrates the boundary segmentation of the bladder cavity-tissue interface of the X-axis stretched bladder images of FIG. 32. The boundary segmentation of the bladder cavity-tissue interface is achieved by process block 700 of master algorithm 120 and is shown in red.

FIGS. 34A-B and 31A are linearly interpolated segmentations of bladder phantom ultrasound images determined by Initial Walls in process block 322. The segmented boundary interface along each bladder cavity-tissue interface is shown in white.

FIGS. 35A-B are fast marching-live wire segmentations of bladder phantom ultrasound images in relation to the same bladder images of the X-axis stretched images of FIGS. 34A-B. The segmented boundary interface along each bladder cavity-tissue interface is shown in white. In general there is more accurate segmentation in that there is less overlap into the echogenic, tissue-simulated regions and the extracted close contours are smoother with the fast marching-live wire segmentations than with the linearly interpolated segmentation.

Figure 36C:
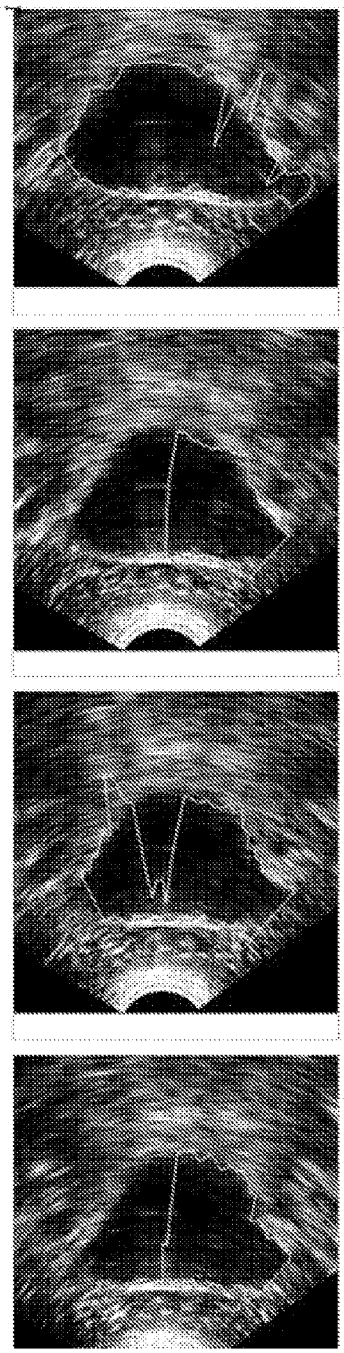

FIGS. 36A-C is a series of Cartesian bladder images segmented by non-dynamic programming algorithms. In these series the non-dynamic algorithms involves initial walls of process block 322. The segmentation of the bladder boundary interface is shown in white and in general is jagged, overlaps into surrounding echogenic tissue, and in some cases, substantially undercuts into the lumen space of the bladder cavity.

Figure 37C:
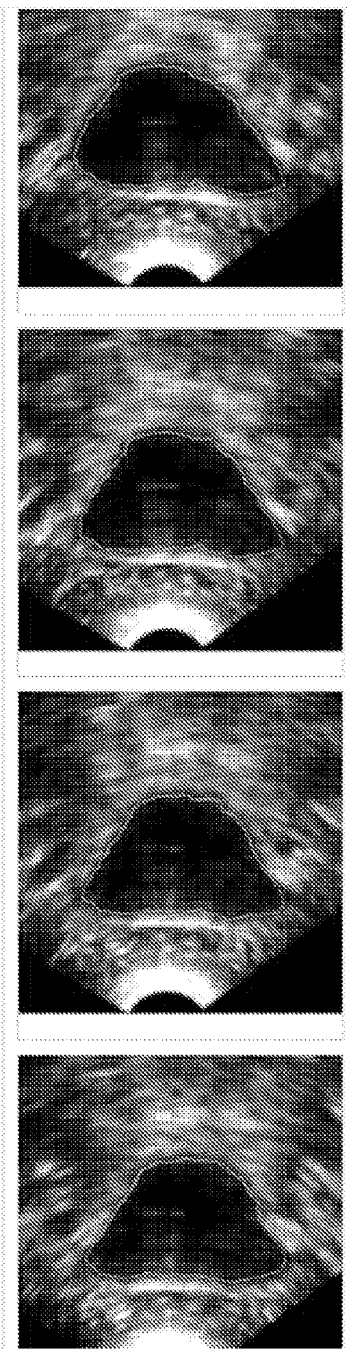

FIGS. 37A-C is a series of Cartesian bladder images segmented by the dynamic programming algorithms of processing block 300 illustrated in FIG. 7. The segmentation of the bladder boundary interface is shown in white or light blue, and in general is smooth, does not significantly overlaps into echogenic tissue, nor exhibits undercuting into the lumen space of the bladder cavity.

FIGS. 38-41 below are based on the 3D level set actove contour method.

Figure 38:
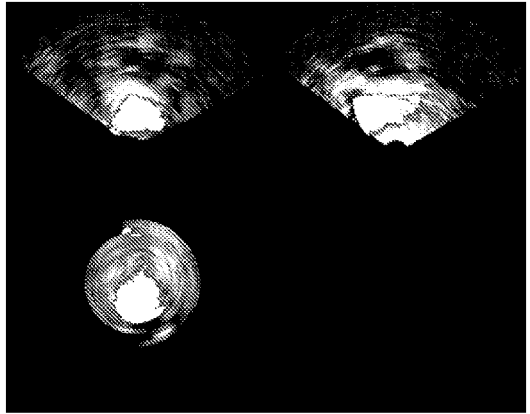
FIG. 38 is a three-panel Cartesian abdominal aorta image that has been adjusted under level-set thresholds.
Figure 39:
FIG. 39 is a three-panel Cartesian abdominal aorta 3D image that has undergone a Euclidian Distance Transform (EDT)

FIG. 38 is s a three-panel Cartesian abdominal aorta image that has been adjusted under level-set thresholds to make a high contrast, skeletal image per sub-algorithm 800 detailed in FIG. 25. The tubular cavity-tissue segmentation interface of these 2D scanplanes is amplified to show the cavity-tissue demarcation.FIG. 39 is a three-panel Cartesian abdominal aorta 3D image that has undergone a Euclidian Distance Transform (EDT).

Figure 40:
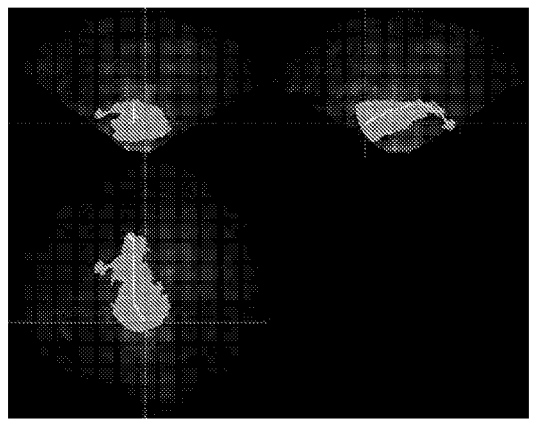
FIG. 40 is the three-panel Cartesian, Euclidian Distance Transformed image to which perpendicular planes are extracted along the centerline.
Figure 41:
FIG. 41 is another view, amplified, of the three-panel Cartesian, Euclidian Distance Transformed image of FIG. 36.

FIG. 40 is the three-panel Cartesian, Euclidian Distance Transformed image to which perpendicular planes are extracted along the centerline. Here the perpendicular planes indicate circular-like regions emanating from the tubular interface of the abdominal aorta, suggesting a possible aneurysm to be reported per sub-algorithm 800. FIG. 41 is another view, amplified, of the three-panel Cartesian, Euclidian Distance Transformed image of FIG. 36. Circular regions along the abdominal aorta are seen radiating approximately perpendicular to the centerline drawn through the abdominal aorta—further indicating a possible aneurysm condition.

While the particular embodiments for systems and methods have been illustrated and described for presenting and determining the shape ultrasound acquired other non-ultrasound imaging systems may employ the ultrasound method algorithms adapted to the non-ultrasound imaging modalities, for example, x-ray based computer tomography scans. Accordingly, the scope of embodiments of the invention is not limited by the disclosure of the particular embodiments. Instead, embodiments of the invention should be determined entirely by reference to the claims that follow.

The embodiments of the invention in which an exclusive property or privilege is claimed are defined as follows:

1. A method for ultrasonic imaging of a region-of-interest within a subject, comprising the steps of:
   exposing the region-of-interest to ultrasound energy generated by an ultrasonic transceiver emitting an ultrasound frequency acoustically coupled to and placed against a surface location of the subject;
   collecting ultrasound echoes with the ultrasonic transceiver from tissue at least partially surrounding a cavity in the region-of-interest;
   generating a first set of tissue pixel candidate points occupying regions near a cavity-tissue interface;
   generating successive sets of tissue pixel candidate points by:
   (a) determining a next subsequent set of tissue pixel candidate points based upon extracting positional information from a cost function analysis of the first set,
   (b) identifying said next subsequent set as a previous subsequent set,
   (c) determining a next subsequent set of tissue pixel candidate points based upon extracting positional information from a cost function analysis of the previous subsequent set, and
   (d) repeating steps (b)-(c) in an iterative manner until the occurrence of a predetermined condition; and
   determining a boundary contour between the cavity-tissue interface based upon the successive sets of tissue pixel candidate points.

2. The method of claim 1, wherein exposing the region-of-interest includes repositioning the transceiver in relation to the region-of-interest from the positional information of the cavity presented on the display.

3. The method of claim 2, wherein exposing the region-of-interest is modified by algorithms executed by a computer readable medium operated by a microprocessor device in signal communication with the display and the transceiver.

4. The method of claim 3, wherein the positional information of the cavity is conveyed to directional indicators associated with the transceiver to direct a user to a subsequent surface location of the subject to reposition the transceiver for re-exposing the region-of-interest with ultrasound energy.

5. The method of claim 1, wherein determining the boundary contour between the cavity-tissue interface utilizing the cost function analysis is governed by the shape of the cavity, including shapes having a substantially spherical and substantially cylindrical appearance.

6. A system for ultrasonic imaging of a region-of-interest within a subject, comprising:
   an ultrasound transceiver configured to deliver ultrasound pulses having a fundamental frequency and to acquire ultrasound echoes returning from tissue at least partially surrounding a cavity in the region-of-interest;
   a microprocessor device in signal communication with the transceiver; and
   a computer readable medium having executable instructions thereon configured to:
   generate a first set of tissue pixel candidate points occupying regions near a cavity-tissue interface;
   generate successive sets of tissue pixel candidate points by:

(a) determining a next subsequent set of tissue pixel candidate points based upon extracting positional information from a cost function analysis of the first set,
(b) identifying said next subsequent set as a previous subsequent set,
(c) determining a next subsequent set of tissue pixel candidate points based upon extracting positional information from a cost function analysis of the previous subsequent set, and
(d) repeating steps (b)-(c) in an iterative manner until the occurrence of a predetermined condition; and
determine a boundary contour between the cavity-tissue interface based upon the first and successive sets of pixel candidate points.

7. The system of claim 6, wherein determining the boundary contour between the cavity-tissue interface is governed by the shape of the cavity, including shapes having a substantially spherical and substantially cylindrical appearance.

* * * * *